(12) United States Patent
Tanaka et al.

(10) Patent No.: US 8,579,883 B2
(45) Date of Patent: Nov. 12, 2013

(54) BODY-INSERTABLE APPARATUS AND MEDICAL AGENT DISCHARGE METHOD

(75) Inventors: Shinsuke Tanaka, Hachioji (JP);
Hironobu Takizawa, Hachioji (JP);
Hironao Kawano, Hachioji (JP)

(73) Assignee: Olympus Corporation, Tokyo (JP)

( * ) Notice: Subject to any disclaimer, the term of this patent is extended or adjusted under 35 U.S.C. 154(b) by 317 days.

(21) Appl. No.: 12/140,004

(22) Filed: Jun. 16, 2008

(65) Prior Publication Data

US 2008/0255543 A1 Oct. 16, 2008

Related U.S. Application Data

(63) Continuation of application No. PCT/JP2006/324973, filed on Dec. 14, 2006.

(30) Foreign Application Priority Data

Dec. 16, 2005 (JP) .................................. 2005-363920

(51) Int. Cl.
*A61K 9/22* (2006.01)

(52) U.S. Cl.
USPC ...................................... 604/890.1; 604/132

(58) Field of Classification Search
USPC ............ 604/93.01, 103.01–103.03, 104–109, 604/151, 153, 164.01, 173, 174, 890.1, 604/891.1, 131–133, 141–143, 145–147; 128/897, 898, 899
See application file for complete search history.

(56) References Cited

U.S. PATENT DOCUMENTS

| | | | |
|---|---|---|---|
| 4,346,698 A * | 8/1982 | Hanson et al. | 600/18 |
| 5,279,607 A | 1/1994 | Schentag et al. | |
| 5,318,557 A | 6/1994 | Gross | |
| 5,693,029 A * | 12/1997 | Leonhardt | 604/264 |
| 7,338,468 B2 * | 3/2008 | Freyman | 604/103.01 |
| 2003/0083645 A1 * | 5/2003 | Angel et al. | 604/890.1 |
| 2003/0181788 A1 | 9/2003 | Yokoi et al. | |
| 2004/0153048 A1 * | 8/2004 | Vigil et al. | 604/509 |
| 2005/0124875 A1 | 6/2005 | Kawano et al. | |
| 2005/0148847 A1 | 7/2005 | Uchiyama et al. | |
| 2005/0267414 A1 * | 12/2005 | Abraham-Fuchs et al. | 604/173 |
| 2006/0200083 A1 * | 9/2006 | Freyman et al. | 604/181 |

FOREIGN PATENT DOCUMENTS

| | | |
|---|---|---|
| CN | 1120852 A | 4/1996 |
| JP | 55-166142 | 12/1980 |
| JP | 57-39776 | 8/1982 |
| JP | 58-19232 | 2/1983 |
| JP | 05-056912 | 3/1993 |
| JP | 06-105847 | 4/1994 |

(Continued)

OTHER PUBLICATIONS

Extended Supplementary European Search Report dated Nov. 5, 2009.

*Primary Examiner* — Kami A Bosworth
(74) *Attorney, Agent, or Firm* — Scully, Scott, Murphy & Presser, P.C.

(57) ABSTRACT

A body-insertable apparatus according to an aspect of the present invention is introduced into a subject to inject medical agent stored in a casing into a desired part in the subject. The body-insertable apparatus includes a fixing unit which fixes the casing to the desired part; and a projecting unit which projects, from the casing, an injection needle for injecting the medical agent. The fixing unit and the projecting unit are driven by a driving source.

6 Claims, 28 Drawing Sheets

(56) References Cited

FOREIGN PATENT DOCUMENTS

| | | |
|---|---|---|
| JP | 8-503384 | 4/1996 |
| JP | 2003-325438 | 11/2003 |
| JP | 2005-160871 | 6/2005 |
| WO | WO 92/21307 | 12/1992 |
| WO | WO 94/24263 A1 | 10/1994 |
| WO | WO 97/02859 A | 1/1997 |
| WO | WO 2004/066903 A | 8/2004 |
| WO | WO 2005/030114 A1 | 4/2005 |
| WO | WO 2006/077529 A | 7/2006 |
| WO | WO 2006/131522 A | 12/2006 |

* cited by examiner

BODY-INSERTABLE APPARATUS AND MEDICAL AGENT DISCHARGE METHOD

CROSS-REFERENCE TO RELATED APPLICATIONS

This application is a continuation of PCT international application Ser. No. PCT/JP2006/324973 filed Dec. 14, 2006 which designates the United States, incorporated herein by reference, and which claims the benefit of priority from Japanese Patent Application No. 2005-363920, filed Dec. 16, 2005, incorporated herein by reference.

BACKGROUND OF THE INVENTION

1. Field of the Invention

The present invention relates to a body-insertable apparatus which is introduced into a subject and includes a local injection mechanism for injecting medical agent, etc. into a desired part in this subject, and a medical agent injection method therefor.

2. Description of the Related Art

In the past, a body-insertable that collects body fluids, etc. of patients has been proposed. This body-insertable apparatus includes a storage chamber and an input control mechanism, in a capsule-type casing. The storage chamber stores body fluids, etc. collected from the inside of the subject. The input control mechanism controls input of the body fluids, etc. into the storage chamber. Such a body-insertable apparatus collects body fluids, etc. under the predetermined control of the input control mechanism at the stage that it arrived at the desired part in the subject, such as a patient, etc., and stores the collected body fluids, etc. in the storage chamber.

A proposed, concrete example of such a conventional body-insertable apparatus includes a collecting needle, a driving mechanism and an input control mechanism (see, for example, Japanese Published Examined Application No. 57-39776). The collecting needle includes an absorbent collecting unit provided at the pointed end thereof. The driving mechanism takes in and out the collecting needle from the casing. The input control mechanism controls operations for projecting and storing the collecting needle by a driving mechanism using an electromagnetic force. The driving mechanism of this body-insertable apparatus projects the collecting needle from the casing, and adheres body fluids or the like to the collecting unit at the pointed end of the collecting needle, under the control of the input control mechanism. After that, the mechanism stores the collecting needle together with the collecting unit to which body fluids or the like are adhered, in the casing. As described above, the body-insertable apparatus collects body fluids or the like at the desired part in the subject.

A body-insertable apparatus which directly supplies a diseased part in the subject with medical agent, by application of the above-described mechanism has been proposed. In this case, the body-insertable apparatus includes an injection needle in place of the collecting needle of the body-insertable apparatus described, for examples in Japanese Published Examined Application No. 57-39776, and is configured to project the injection needle from the casing so as to inject medical agent into the diseased part. Such a body-insertable apparatus is generally miniaturized and lightweighted in order to enhance the portability and its introduction into the subject.

SUMMARY OF THE INVENTION

A body-insertable apparatus according to an aspect of the present invention is introduced into a subject to inject medical agent stored in a casing into a desired part in the subject, and includes a fixing unit which fixes the casing to the desired part; and a projecting unit which projects, from the casing, an injection needle for injecting the medical agent. The fixing unit and the projecting unit are driven by a driving source.

A medical agent injection method according to another aspect of the present invention includes introducing a body-insertable apparatus into a desired part in a subject, the body-insertable apparatus having, inside a casing, medical agent and an injection needle for injecting the medical agent; projecting the injection needle from the casing by a driving source; fixing the body-insertable apparatus to the desired part in the subject by the driving source; and injecting the medical agent into the desired part in the subject using the injection needle projected from the casing.

A medical agent injection method according to still another aspect of the present invention includes introducing a body-insertable apparatus into a desired part in a subject, the body-insertable apparatus having, inside a casing, medical agent and an injection needle for injecting the medical agent; fixing the body-insertable apparatus to the desired part in the subject; projecting the injection needle from the casing, by a driving source; and injecting the medical agent into the desired part in the subject using the injection needle projected from the casing.

A medical agent injection method according to still another aspect of the present invention includes introducing a body-insertable apparatus into a desired part in a subject, the body-insertable apparatus having, inside a casing, medical agent and an injection needle for injecting the medical agent; projecting the injection needle from the casing while fixing the body-insertable apparatus to the desired part in the subject, by a driving source; and injecting the medical agent into the desired part in the subject using the injection needle projected from the casing.

The above and other objects, features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

A body-insertable apparatus and medical agent injection method according to preferred embodiments of this invention will now specifically be explained with reference to the drawings. The embodiments are not to be construed as limiting the invention.

Figure 1:
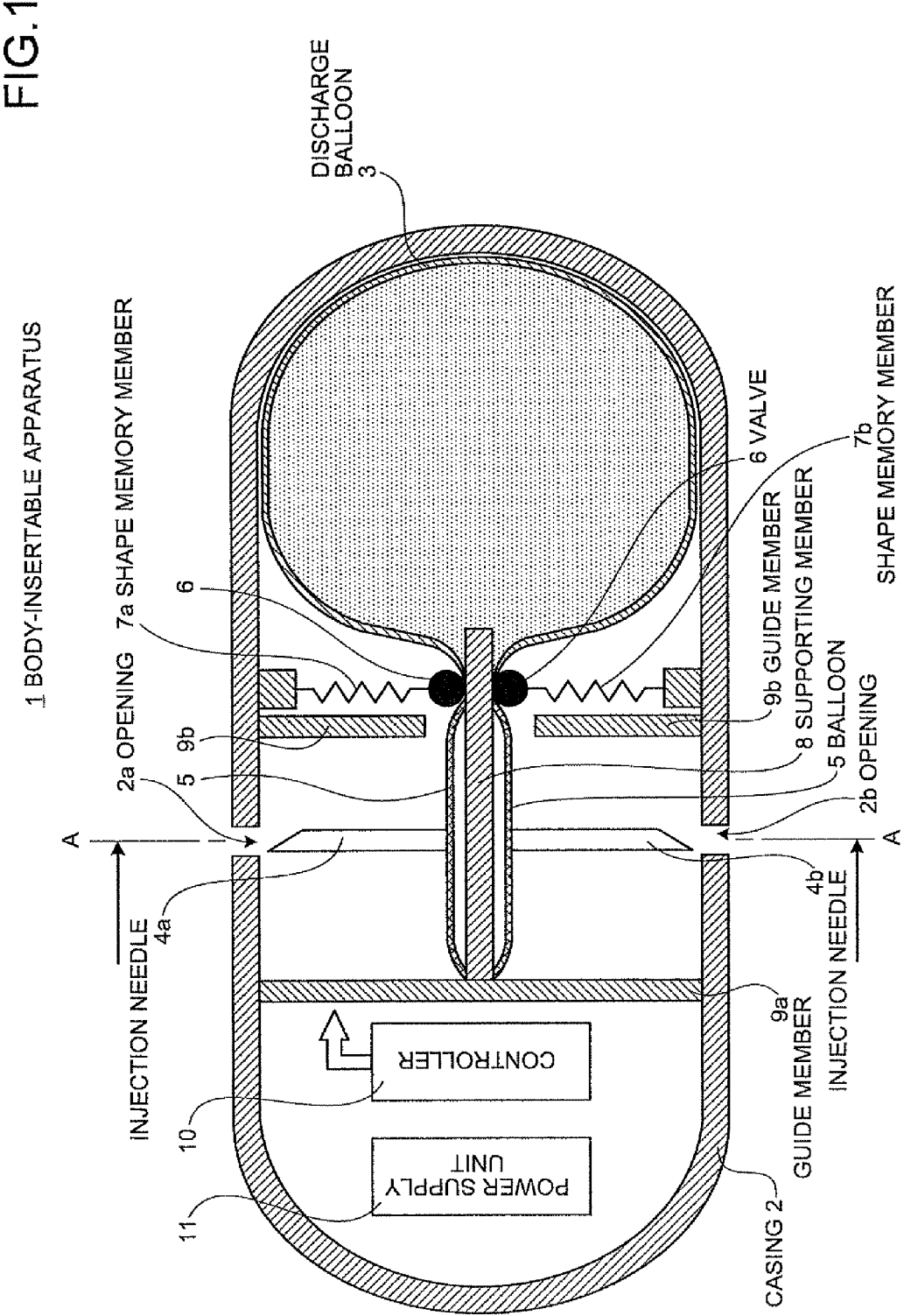
FIG. 1 is a schematic cross sectional view of a configuration example of a body-insertable apparatus as an a first embodiment of this invention.
Figure 2:
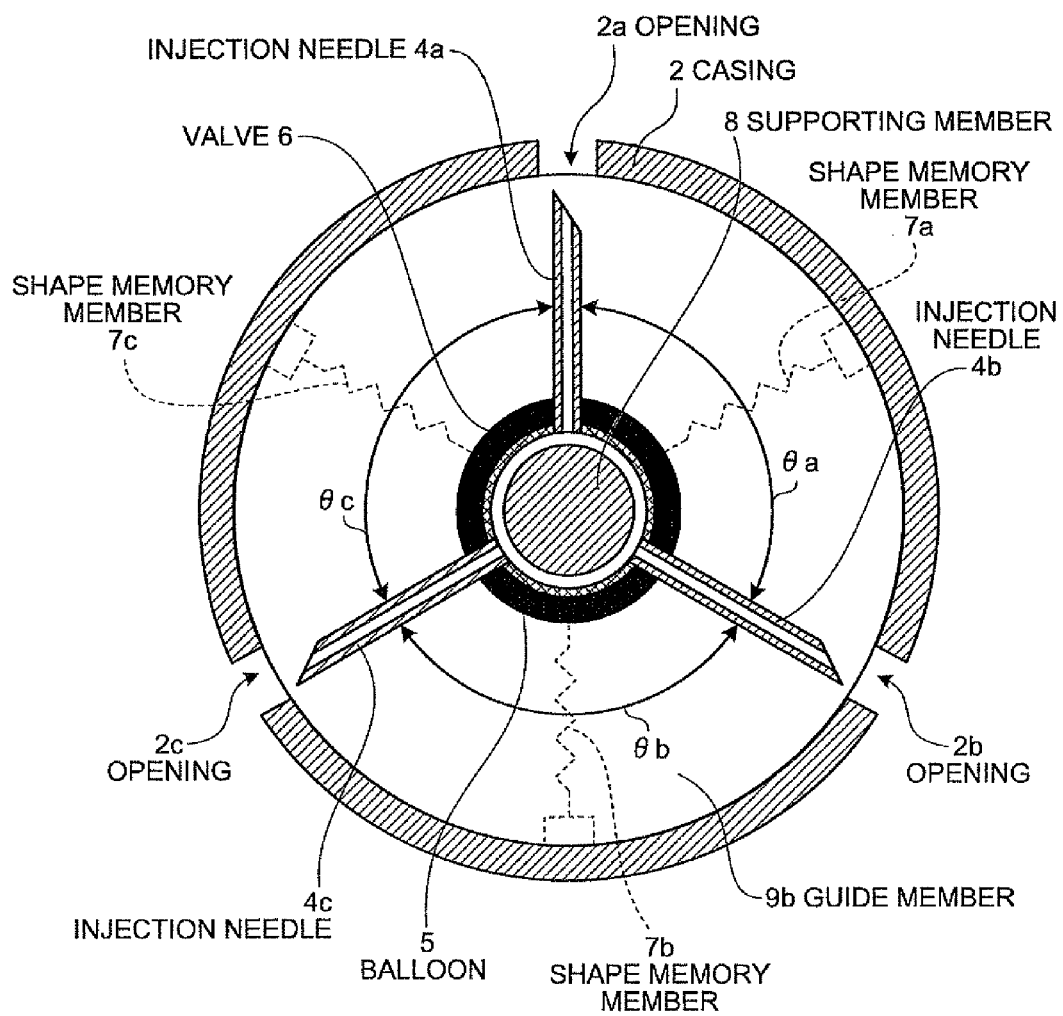
FIG. 2 is a schematic cross sectional view taken along line A-A of the body-insertable apparatus shown in FIG. 1.

FIG. 1 is a schematic cross sectional view schematically showing a configuration example of a body-insertable apparatus as a first embodiment of this invention. FIG. 2 is a schematic cross sectional view taken along a line A-A of the body-insertable apparatus shown in FIG. 1. This body-insertable apparatus 1 is introduced into a subject, such as a patient, etc., and is to inject medical agent into a desired part of the subject, such as a patient, etc. Such a body-insertable apparatus 1 includes a local injection mechanism for injecting medical agent into a capsule-type casing 2 with such a size as to easily be swallowed by a subject. Specifically, as shown in FIG. 1 and FIG. 2, the body-insertable apparatus 1 has a discharge balloon 3, a plurality of injection needles 4a to 4c, and a balloon 5, inside the casing 2. The discharge balloon 3 forms a storage chamber for storing medical agent and discharges the medical agent. The plurality of injection needles 4a to 4c inject the medical agent discharged by the discharge balloon 3 into a desired part in the subject. The balloon 5 is to project the plurality of injection needles 4a to 4c from the casing 2. The body-insertable apparatus 1 has a valve 6 for adjusting a connecting state between the discharge balloon 3 and the balloon 5, shape memory members 7a to 7c for opening/closing the valve 6 and a supporting member 8 for supporting the discharge balloon 3 and the balloon 5. Further, the body-insertable apparatus 1 has guide members 9a and 9b for controlling the expansion direction of the balloon 5, a controller 10 controlling driving of the shape memory members 7a to 7c so as to control the valve 6 to be open/close-driven, and a power supply unit 11 for supplying the controller 10 with driving power. The casing 2 includes a plurality of openings 2a to 2c for inserting the respective injection needles 4a to 4c.

The discharge balloon 3 is to discharge medical agent to be injected into a desired part in the subject. Specifically, the discharge balloon 3 is realized with an elastic member, such as rubber, etc., expanded upon injection of medical agent thereinto, and contains medical agent while maintaining this expansion state. An opening of the discharge balloon 3 (i.e. discharge port) is connected to the opening of the balloon 5, and the periphery of the discharge port is sandwiched between the valve 6 and the supporting member 8. Such a discharge balloon 3 is changed to a state where it is connected to the balloon 5 by the open driving of the valve 6 as will be described later so as to discharge medical agent into the internal space of the balloon 5. In this case, the discharge balloon 3 stores medical agent, and applies pressure to the medical agent by its contraction force (potential to it while storing the medical agent) so as to discharge it.

The injection needles 4a to 4c are to inject the medical agent discharged by the discharge balloon 3 into a desired part in the subject. Each of the injection needles 4a to 4c includes a line for connecting the end side (pointed side) puncturing the subject and the base end side, and is so installed into the balloon 5 as to connect this line and the internal space of the balloon 5. Such injection needles 4a to 4c are taken in and out to and from the casing 2 through the respective openings 2a to 2c. Specifically, the injection needles 4a to 4c are projected to the outside of the casing 2 by the expansion effect of the balloon 5, and are stored inside the casing 2 by the contraction effect of the balloon 5 afterwards.

Each of the injection needles 4a to 4c functions also as fixing means for fixing the casing 2 into a desired part, when puncturing a desired part in the subject. Specifically, the injection needles 4a to 4c pierce and/or push each position in the subject, and resist a reaction occurring from the subject toward the injection needles 4a to 4c, and fix the position of the casing 2 to the desired part of the subject. For example, when the injection needle 4a punctures the desired part in the subject, the rest of the injection needles 4b and 4c are projected into a direction at an angle of 90 degrees or more from the projection direction of this injection needle 4a so as to puncture each position in the subject, resist a reaction occurring from the subject side toward the injection needle 4a, and fix the position of the casing 2 into the desired part. This applies also to the case when the injection needles 4b and 4c puncture the desired part in the subject.

Such injection needles 4a to 4c are so preferably arranged on the balloon 5 as to attain 90 degrees or more angles of θa, θb and θc (see FIG. 2) that are formed with the supporting member 8, as their central axis. Further, the angles θa, θb and θc are desirably approximately the same angles. The angles θa, θb and θc are angles between the injection needle puncturing a desired part in the subject and the rest of injection needles fixing the position of the casing 2. Thus, when 5 or more injection needles are installed onto the balloon 5, of these 5 or more injection needles, angles of 90 or more degrees may be formed among each of the injection needles satisfying the relationship between the above-described injection needle and the fixing means.

The balloon 5 functions as projection means for projecting the injection needles 4a to 4c from the casing 2 using pressure of medical agent as a driving source. Specifically, the balloon 5 is realized with an elastic member, such as rubber, etc., and is supported by the supporting member 8 in a state where its one end is open. This opening is connected to the discharge port of the discharge balloon 3. The periphery of the connection between the opening of this balloon 5 and the discharge port of the discharge balloon 3 is sandwiched between the valve 6 and the supporting member 8, as described above, and the connection state between the internal space of the balloon 5 and the internal space of the discharge balloon 3 is adjusted by the open/close driving of this valve 6. On this balloon 5, as described above, the injection needles 4a to 4c are installed. The balloon 5 expands by pressure of medical agent discharged from the discharge balloon 3 as a driving source so as to project the injection needles 4a to 4c from the casing 2. In this case, the balloon 5 projects the injection needles 4a to 4c having both a function for injecting medical agent into a desired part in the subject and a function as the above-described fixing means, for example, in the radial direction of the casing 2 approximately at the same time. Such injection needles 4a to 4c are projected from the casing 2 toward the walls of the alimentary tract in the subject. That is, the balloon 5 functions as a mechanism for projecting the injection needles 4a to 4c and also functions as a mechanism for driving the rest of the injection needles 4a to 4c as the above-described fixing means. Such a balloon 5 is formed of an elastic member with low contraction force as compared with the discharge balloon 3. When the pressure of the medical agent discharged to the internal space of the balloon 5 decreases below the contraction force of the balloon 5, the balloon 5 contracts and stores the injection needles 4a to 4 inside the casing 2.

It is preferred that each of installation elements of the balloon 5 that install such injection needles 4a to 4c be reinforced with a resin member or a plate-like member, etc., and be formed hard as compared with the balloon body except for the installation elements. As a result, the balloon 5 can prevent that the injection needles 4a to 4c are pushed back to the balloon 5 side due to a reaction toward the injection needles 4a to 4c projected from the casing 2.

The valve 6 and the shape memory members 7a to 7c form a connection adjustment mechanism for adjusting the connection state between the internal space of the discharge balloon 3 and the internal space of the balloon 5. Specifically, the valve 6 is realized with a ring-like shaped elastic member, and is fit onto the supporting member 8 via the above-described periphery of the connection between the discharge balloon 3 and the balloon 5. In this case, the valve 6 presses this periphery of the connection to the supporting member 8 thereby controlling the discharge port of the discharge balloon 3 to be in a closed state, and interrupts the connection between the internal space of the discharge balloon 3 and the internal space of the balloon 5. The valve 6 is open-driven by the effect of the shape memory members 7a to 7c, controls the discharge port of the discharge balloon 3 to be in an open state, and attains the connection state between the internal space of the discharge balloon 3 and the internal space of the balloon 5.

The shape memory members 7a to 7c are to change the position of the valve 6 in relation to the supporting member 8, i.e. the "open/close" state of the valve 6. Specifically, the shape memory members 7a to 7c have a rod-like or coil-like (e.g. SMA coil) structure, have predetermined shape memory properties, and are formed of a shape memory alloy having a predetermined electrical resistance value. One ends of such shape memory members 7a to 7c are fixed onto the casing 2, while the other ends thereof are fixed onto the valve 6. The shape memory members 7a to 7c have such a sufficient length as to fit the valve 6 onto the supporting member 8 under the same temperature condition as the temperature in the subject, for example. The shape memory members 7a to 7c change their shape under the temperature condition that is sufficiently high as compare to the temperature in the subject, for example, and function for isolating the valve 6 from the supporting member 8 (i.e. to reset the state where the valve 6 is fit onto the supporting member 8). Because the shape is thus changed in accordance with the temperature, the shape memory members 7a to 7c change the valve 6 into an open state or a close state.

The guide members 9a and 9b are to control the expansion direction of the balloon 5. Specifically, the guide the members 9a and 9b are so installed on the casing 2 as to be positioned near the edge part of the balloon 5, and control the expansion direction of the balloon 5 such that the injection needles 4a to 4c are projected from the casing 2 respectively through the openings 2a to 2c.

The controller 10 controls the shape change of the shape memory members 7a to 7c depending on as to whether an electric current is supplied to the shape memory members 7a to 7c, and controls the open/close driving of the valve 6 through the controlling of this shape change. Specifically, the controller 10 supplies the shape memory members 7a to 7c with an electrical current when the body-insertable apparatus 1 introduced into the subject has reached a desired part in the subject, thereby changing the shape of the shape memory members 7a to 7c so as to control the valve 6 to be open-driven. The controller 10 stops supplying the shape memory members 7a to 7c with an electrical current so as to return the shape memory members 7a to 7c in their original shapes, thereby controlling the valve 6 to be close-driven. As described above, the controller 10 controls to start or stop an operation for discharging medical agent with the discharge balloon 3, and controls the projection operation for the injection needles 4a to 4c and the fixing operation for the casing 2 to a desired part in the subject through this controlling of the medical agent discharge operation.

In a configuration for setting the timing to supply, for example, an electrical current in accordance with the controller 10, a timer mechanism may be included, or a radio receiving mechanism may be installed and an external control signal may be supplied to the controller 10.

Figure 3:
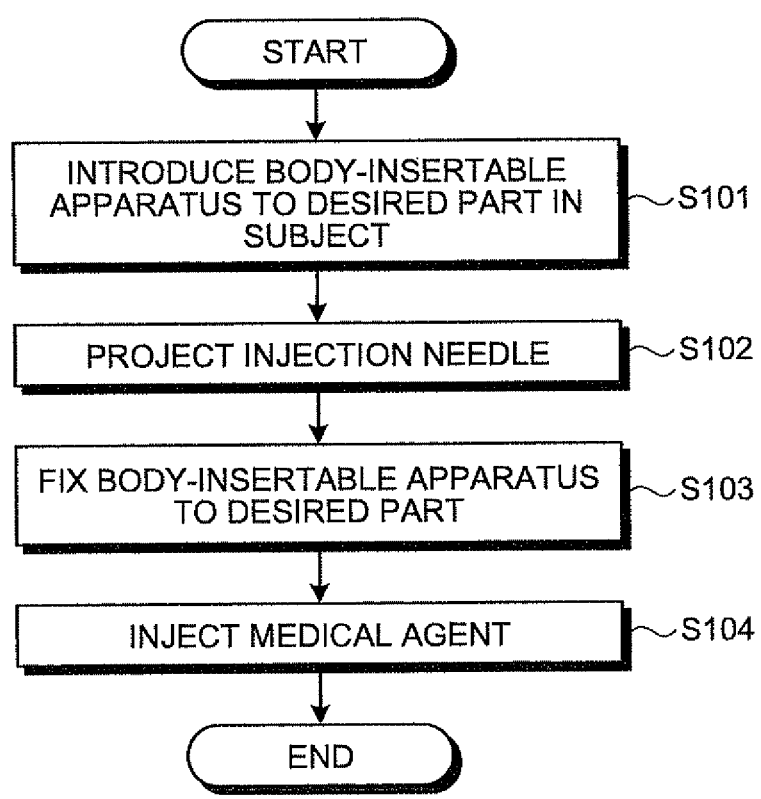
FIG. 3 is a flowchart for explaining a medical agent injection method according to the first embodiment of the present invention.

Descriptions will now be made to a medical agent injection method according to the first embodiment of the present invention. FIG. 3 is a flowchart for explaining the medical agent injection method according to the first embodiment of the present invention. The medical agent injection method will hereinafter be described, by way of example with reference to the case where the medical agent is injected into a desired part in the subject using the body-insertable apparatus 1 according to the first embodiment.

As shown in FIG. 3, the body-insertable apparatus 1 is introduced into a desired part in the subject, such as a patient, etc. (Step S101). Specifically, the body insertable 1 is introduced into the body from the mouth of the subject, and moves inside the internal organs by peristaltic movement so as to reach the desired part (e.g., the diseased part) in the subject.

Through this step S101 (introduction step), the body-insertable apparatus 1 having reached the desired part in the subject projects the injection needles 4a to 4c toward the desired part in the subject (Step S102). In this step S102 (projection step), the injection needles 4a to 4c are projected from the casing 2 by the effect of the balloon 5 which expands by the pressure of medical agent as a driving source.

The body-insertable apparatus 1 makes the injection needles 4a to 4c projected in Step S102 pierce and/or push the desired part in this subject so as to be fixed to this desired part (Step S103). In this step S103 (fixing step), the body-insertable apparatus 1 makes the injection needles 4a to 4c pierce and/or push the desired part in the subject by the effect of the balloon 5 which expands by the same driving source as that in Step S102 (pressure of medical agent). As a result, the casing 2 is fixed to the desired part in the subject, and the injection needles 4a to 4c puncture the desired part.

After that, the body-insertable apparatus 1 injects the medical agent into the desired part in the subject through the injection needles 4a to 4c, in the state where the injection needles 4a to 4c puncture the desired part in the subject (Step S104). In this step S104, the body-insertable apparatus 1 opens the valve 6 so as to inject the medical agent inside the discharge balloon 3 into the desired part in the subject through the injection needles 4a to 4c. As described, the body-insertable apparatus 1 attains the medical agent injection process for the desired part in the subject.

Figure 4:
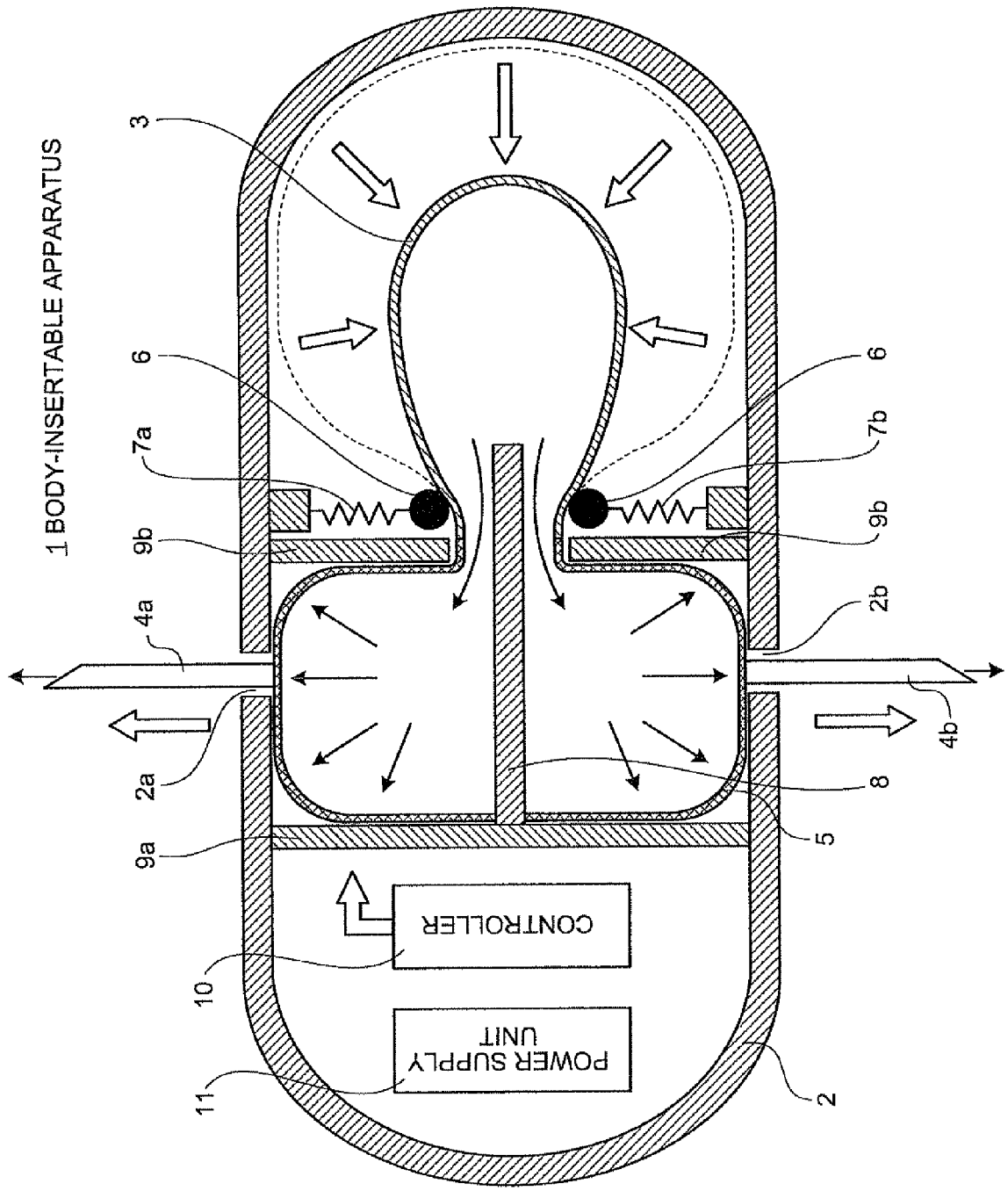
FIG. 4 is a schematic cross sectional view for explaining a projection operation of an injection needle by a balloon by medical agent pressure as a driving source.
Figure 5:
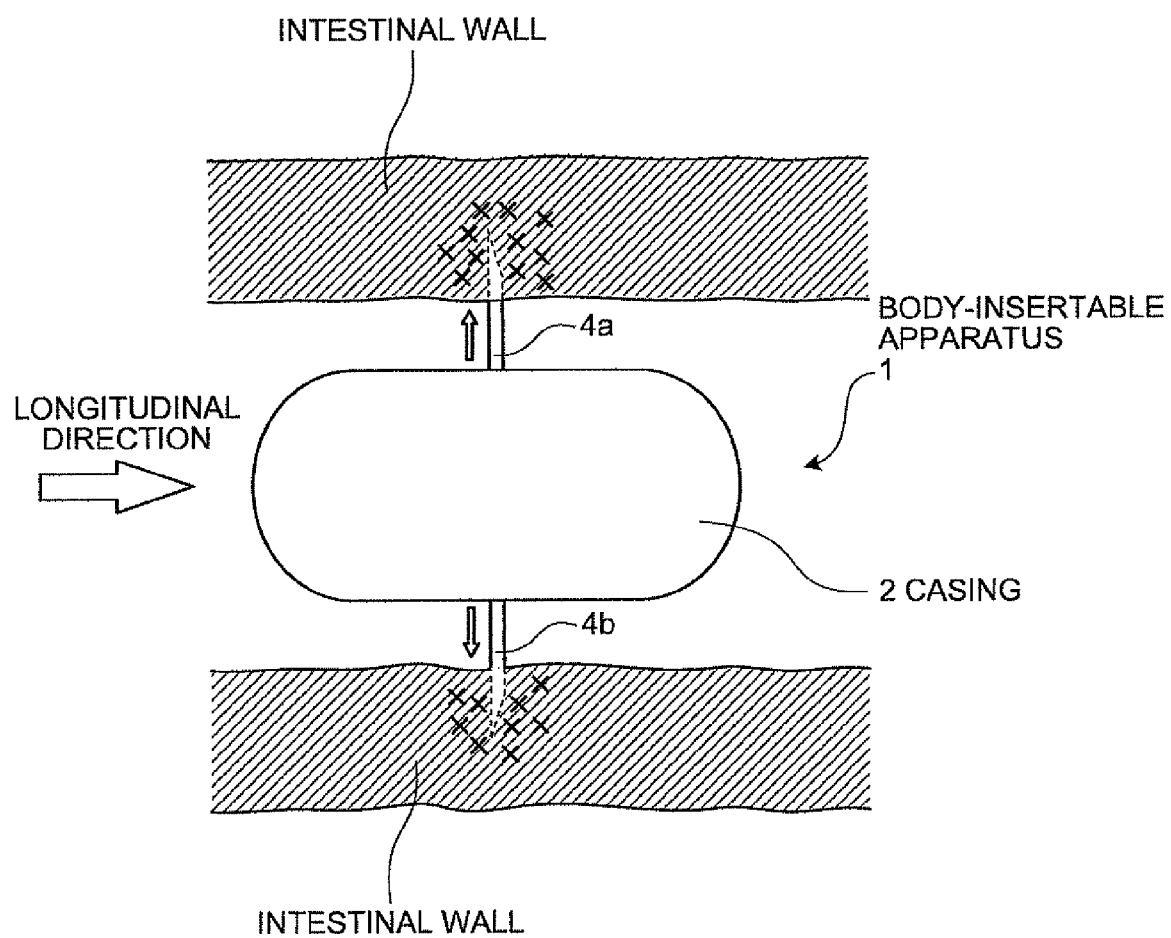
FIG. 5 is a schematic diagram exemplarily showing a state wherein the casing is fixed to a desired part in a subject.
Figure 6:
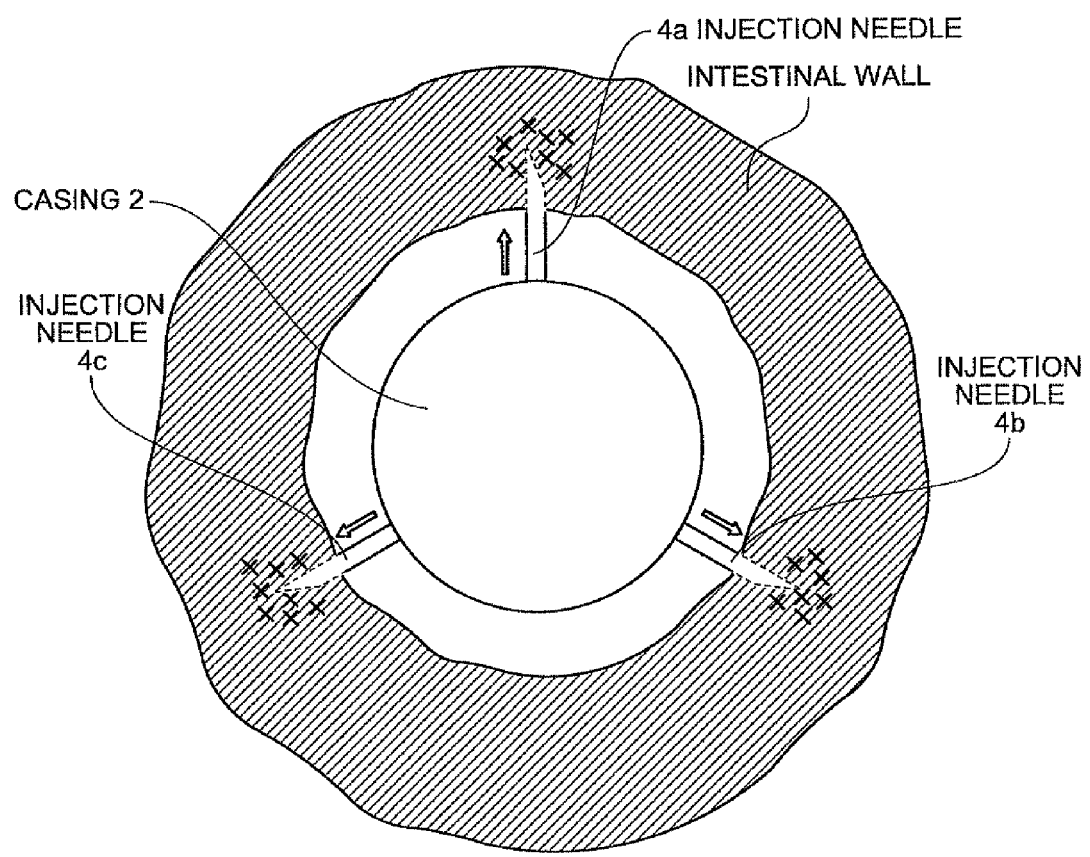
FIG. 6 is a front schematic diagram showing the body-insertable apparatus shown in FIG. 5, viewed from the longitudinal direction.

Next, descriptions will now be made to an operation of the balloon 5 using pressure of medical agent discharged by the discharge balloon 3 as a driving source. FIG. 4 is a schematic cross sectional view for explaining a projection operation for the injection needles 4a to 4c by the balloon 5 using pressure of medical agent as a driving source. FIG. 5 is a schematic diagram exemplarily showing a state where the casing 2 is fixed to a desired part in the subject. FIG. 6 is a front schematic diagram showing the body-insertable apparatus 1 shown in FIG. 5, viewed from the longitudinal direction. Note that the injection needles 4a to 4c function as fixing means for fixing the casing 2, as described above. Thus, the projection operation by this balloon 5 includes a fixing operation for fixing the casing 2 to the desired part in the subject. Descriptions will now be made to the operation of the balloon 5 with reference to FIG. 4 to FIG. 6.

The controller 10 supplies the shape memory members 7a to 7c with an electrical current, when the body-insertable apparatus 1 introduced into the subject has reached a desired part in the subject, and allows the shape memory members 7a to 7c to generate Joule heat. The shape memory members 7a to 7c with temperatures increased to a predetermined value or higher by the Joule heat are changed in their shapes in such a direction as to separate the valve 6 with respect to the supporting member 8 so as to control the valve 6 to be open-driven. In this case, the shape memory members 7a to 7c make a contraction change so as to control the valve 6 to be open-driven.

The discharge port of the discharge balloon 3 opens, and the internal space of the discharge balloon 3 and the internal space of the balloon 5 are connected to each other, due to the open driving of the valve 6. In this case, the discharge balloon 3 begins a contraction operation for applying pressure to medical agent and begins an operation for discharging the medical agent. The medical agent discharged by this discharge balloon 3 flows into the internal space of the balloon 5 and applies pressure to the balloon 5.

The balloon 5 expands by the pressure of the medical agent as a driving source, so as to implement a projection operation for projecting the injection needles 4a to 4c from the casing 2. Specifically, the balloon 5 projects the injection needles 4a to 4c respectively from the openings 2a to 2c of the casing 2, and pierces and/or pushes the intestinal wall in the subject with the injection needle 4a to 4c, thereby fixing the position of the casing 2 into the desired part in the subject and puncturing the desired part (e.g. diseased part in the intestines) with the injection needles 4a to 4c. In this case, the balloon 5 resists a reaction occurring from the intestinal wall toward the injection needles 4a to 4c so as to project the injection needles 4a to 4c when puncturing the desired part in the subject. Thus, the balloon 5 prevents that the casing 2 is moved by this reaction, and the injection needles 4a to 4c can easily puncture the desired part in the subject.

In the state where such injection needles 4a to 4c puncture the desired part in the subject, the medical agent discharged by the discharge balloon 3 circulates sequentially through the balloon 5 and the injection needles 4a to 4c, and are injected to the desired part in the subject as shown in FIG. 5 and FIG. 6. The state where the medical agent is injected to the desired part remains, until the contraction force of the discharge balloon 3 will be zero, or the valve 6 is close-driven under the control of the controller 10. As a result, a desired amount of medical agent can be injected into the desired part in the subject.

After that, when the pressure of medical agent decreases to the contraction force of the balloon 5 in accordance with a decrease in the amount of medical agent discharged into the internal space of the balloon 5, the balloon 5 is to pull out the injection needles 4a to 4c from the respective punctured parts by its contraction force, thereby storing the injection needles 4a to 4c inside the casing 2. As a result, after the body-insertable apparatus 1 has completely injected the medical agent into the desired part in the subjects it can move in the alimentary tract in the subject without unintentionally puncturing any other position in the subject.

In the first embodiment of this invention, the body-insertable apparatus having three injection needles has been described by way of example. However, the present invention is not limited to this. Two or more injection needles may be provided in such a relationship that the injection needles respectively correspond to the fixing means for the casing and the injection needle(s).

In the embodiment of this invention, three injection needles also have a function as the fixing means for the casing. However, this invention is not limited to this. One or more needle-like members for fixing the position of the casing by piercing and/or pushing the wall of the alimentary tract in the subject and one or more injection needles may be installed onto the balloon 5 as the fixing means. One or more cylindrical members for fixing the position of the casing by pushing it against the wall of the alimentary tract in the subject and one or more injection needles may be installed onto the balloon 5.

Accordingly, as described above, in the configuration of the first embodiment of this invention, two or more injection needles also having a function as the fixing means for the casing are mounted on the balloon which expands by the pressure of medical agent as a driving source, or one or more injection needle and one or more cylindrical member or needle-like member functioning as the fixing means for the casing are mounted thereon. Such injection needles and the fixing means are projected from the casing by the expansion effect of the balloon, and the casing is fixed to the desired part in the subject using the fixing means piercing and/or pushing the wall of the alimentary tract in the subject. Therefore, the injection needles can be projected by the pressure of medical agent as one driving source, and the casing can be prevented from moving in such a direction that the casing is separated from the desired part when the injection needles pierce and/or push the desired part in the subject, thus promoting miniaturization of the apparatus size and realizing such a body-insertable apparatus whose injection needle(s) can easily be stuck into the desired part in the subject.

The injection needles and the fixing means are stored inside the casing by the contraction effect of the balloon onto which such injection needles and the fixing means are mounted. Therefore, after the process for injecting medical agent into the desired part in the subject is completed, it can move in the subject without unintentionally puncturing any other part in the subject.

Further, because the controller controls the open/close driving of the valve provided in the discharge port for medical agent, the operation for discharging medical agent can begin and stop repeatedly at a desired timing. As a result, the operation for discharging medical agent can intermittently be repeated in a period since it is introduced into the subject until it is discharged to the outside, and desired amounts of medical agent can be injected respectively into a plurality of desired parts in the subject.

Descriptions will now be made to a second embodiment of this invention. A body-insertable apparatus according to the second embodiment has a function for projecting the injection needles and fixing the casing into a desired part in the subject by a medical agent discharging force as one driving force, which is a physical force for discharging the medical agent.

Figure 7:
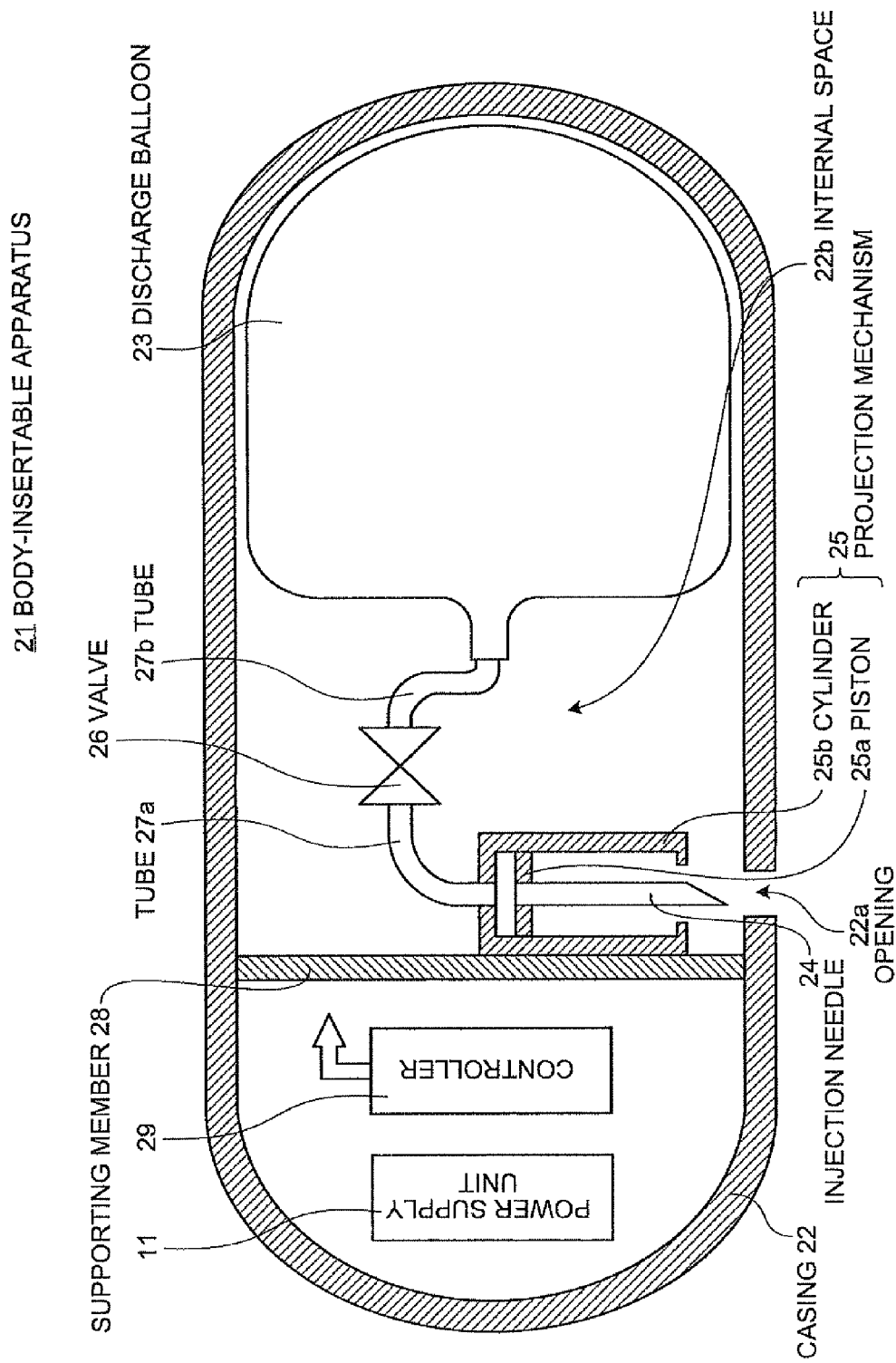
FIG. 7 is a schematic cross sectional view schematically showing a configuration example of a body-insertable apparatus as a second embodiment of this invention.

FIG. 7 is a schematic cross sectional view schematically showing a configuration example of the body-insertable apparatus as the second embodiment of this invention. As shown in FIG. 7, this body-insertable apparatus 21 includes a local injection mechanism for injecting medical agent into capsulate-type casing 22 with such a size as to easily be introduced into a subject. Specifically, the body-insertable apparatus 21 has a discharge balloon 23, an injection needle 24 and a projection mechanism 25, inside such casing 22. The discharge balloon 23 forms a storage chamber for storing medical agent and discharges the medical agent. The injection needle 24 injects the medical agent discharged by the discharge balloon 23 into the desired part in the subject. The projection mechanism 25 projects the injection needle 24 from the casing 22. The body-insertable apparatus 21 has a valve 26, a tube 27a, a tube 27b and a supporting member 28. The valve 26 is open/close-driven in order to begin or start an operation for discharging medical agent by the discharge balloon 23. The tube 27a forms a circulation pipeline for medical agent between the valve 26 and the projection mechanism 25. The tube 27b forms a circulation pipeline for medical agent between the discharge balloon 23 and the valve 26. The supporting member 28 supports the projection mechanism 25 in a predetermined position inside the casing 22. Further, the body-insertable apparatus 21 has a controller 29 controlling the open/close driving of the valve 26, and a power supply unit 11 or supplying the controller 29 with driving power.

As described above, the casing 22 is capsulate-type armored casing with such a size as to easily be introduced by a subject, and includes an opening 22a in a position corresponding to the injection needle 24. The casing 22 contains the discharge balloon 23 in its internal space 22b. This internal space 22b is formed, for example, from a partial area of the casing 22 which includes an area including the opening 22 and the supporting member 28, and is connected to the outside of the casing 22 through the opening 22a. In this case, the opening 22a functions as a projection port for projecting the injection needle 24 and functions also as a suction port for sucking the external of the casing 22 (e.g. gas or living tissue, etc.) when the internal space 22b is depressurized in accordance with the contraction effect of the discharge balloon 23, as will be described later.

The discharge balloon 23 is realized with an elastic member, such as rubber, etc., expands upon injection of medical agent, and stores the medical agent while maintaining this expansion state. In this case, the discharge balloon 23 functions for discharging the stored medical agent by a potential medical agent discharge force due to this expansion, i.e. its contraction force. Specifically, the discharge balloon 23 is connected to the valve 26 through the tube 27b, contracts when the valve 26 is open-driven, and performs the operation for discharging the medical agent upon application of pressure to the medical agent by its contraction force. The discharge balloon 23 stops its contraction when the valve 26 is closed-driven, and stops the operation for discharging the medical agent.

The discharge balloon 23 contracts itself when performing the operation for discharging the medical agent, thereby depressurizing the internal space 22b of the casing 22 and generating a sucking force for sucking the external of the casing 22 (e.g. gas or living tissue, etc.) through the opening 22a of the casing 22. That is, the discharge balloon 23 generates this sucking force based on its own contraction force as an example of the medical agent discharging force for discharging the medical agent. In this case, the discharge balloon 23 sucks the living tissue by thus generated sucking force using the opening 22a as a suction port, and functions as fixing means for fixing the casing 22 to the desired part in the subject.

The projection mechanism 25 is to project the injection needle 24 to the outside of the casing 22. Specifically, the projection mechanism 25 is realized with a piston 25a on which the base end of the injection needle 24 is mounted and a cylinder 25b slidably storing this piston 25a. The cylinder 25b is connected to the valve 26 through the tube 27a connected to its base end, and circulates the medical agent discharged by the discharge balloon 23 to the piston 25a and the line of the injection needle 24 when the valve 26 is open-driven. In this case, the piston 25a slides in the cylinder 25b by the pressure of medical agent discharged into the cylinder 25a through this tube 27a so as to project the injection needle 24 from the opening 22a. This injection needle 24 includes a line connected to the pointed end (pointed side) puncturing the subject and the base end side, and is fixed onto the piston 25a in a state where this line is not blocked up.

The valve 26 is open/close-driven under the control of the controller 29, and adjusts the connection state between the discharge balloon 23 and the cylinder 25b through the tubes 27a and 27b. Specifically, the valve 26 is open-driven so as to connect the discharge balloon 23 to the cylinder 25b, and begins the operation for discharging the medical agent by the discharge balloon 23. The valve 26 is close-driven so as to interrupt the connection between the discharge balloon 23 and the cylinder 25b and stop the operation for discharging the medical agent by the discharge balloon 23.

The controller 29 is to control the open/close driving of the valve 26. Specifically, the controller 29 controls the valve 26 to be open-driven, when the body-insertable apparatus 21 introduced into the subject has reached the desired part in the subject. In this case, the controller 29 controls the operation for discharging medical agent by the discharge balloon 23 and the operation for projecting the injection needle 24 by the projection mechanism 25, through the controlling of the valve 26 to be open-driven. The controller 29 controls the valve 26 to be close-driven, and controls to stop the operation for discharging the medical agent by the discharge balloon 23 through this controlling of the valve 26 to be close-driven. As described, the controller 29 controls the operation for discharging the medical agent by the discharge balloon 23, thereby controlling the operation for projecting the injection needle 24 and the operation for fixing the casing 22 to the desired part in the subject.

In a configuration for setting the timing to control the driving of the valve 26 in accordance with the controller 29, a timer mechanism may be included, for example, or a radio receiving mechanism may be installed and an external control signal may be supplied to the controller 29.

Figure 8:
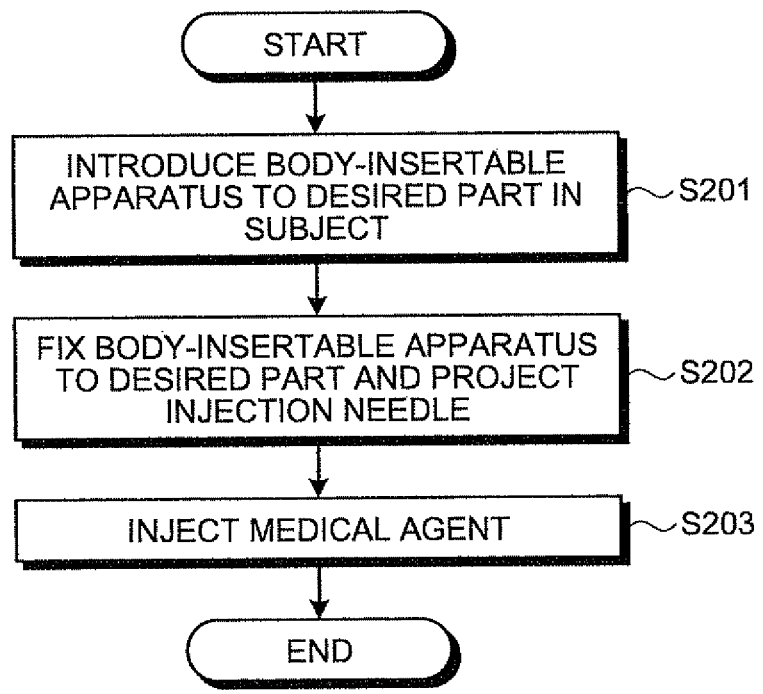
FIG. 8 is a flowchart for explaining a medical agent injection method according to the second embodiment of the present invention.

Descriptions will now be made to a medical agent injection method according to the second embodiment of this invention. FIG. 8 is a flowchart for explaining the medical agent injection method according to the second embodiment of the present invention. The medical agent injection method will hereinafter be described, by way of example with reference to the case where the medical agent is injected to the desired part in the subject by the body-insertable apparatus 21 according to the second embodiment.

As shown in FIG. 8, like the above-described body-insertable apparatus 1 according to the first embodiment, the body-insertable apparatus 21 is introduced to a desired part in a subject, such as a patient, etc. (Step S201), and reaches the desired part (diseased part, etc.) in the subject.

The body-insertable apparatus 21 having reached the desired part in the subject through this step S201 (introduction step) is fixed to the desired part in the subject, and projects the injection needle 24 to the desired part (Step S202). In this step S202, the body-insertable apparatus 21 depressurizes the internal space 22b of the casing 22 and sucks a part of the desired part in the subject toward the side of the internal space 22b, by the contraction force of the discharge balloon 23 as one driving source, thereby fixing the casing to the desired part in the subject and projecting the injection needle 24 from the casing 22 toward this desired part.

After that, the body-insertable apparatus 21 injects medical agent to the desired part in the subject with the injection needle 24 which has been projected from the casing in this step S202 (Step 203). In this step S203, the injection needle 24 pierces and/or pushes the desired part in the subject by the pressure of medical agent based on the contraction force of the discharge balloon 23. The body-insertable apparatus 21 injects the medical agent inside the discharge balloon 23 to the desired part in the subject though the injection needle 24.

Accordingly, the body-insertable apparatus 21 attains the medical agent injection process for the desired part in the subject.

Figure 9:
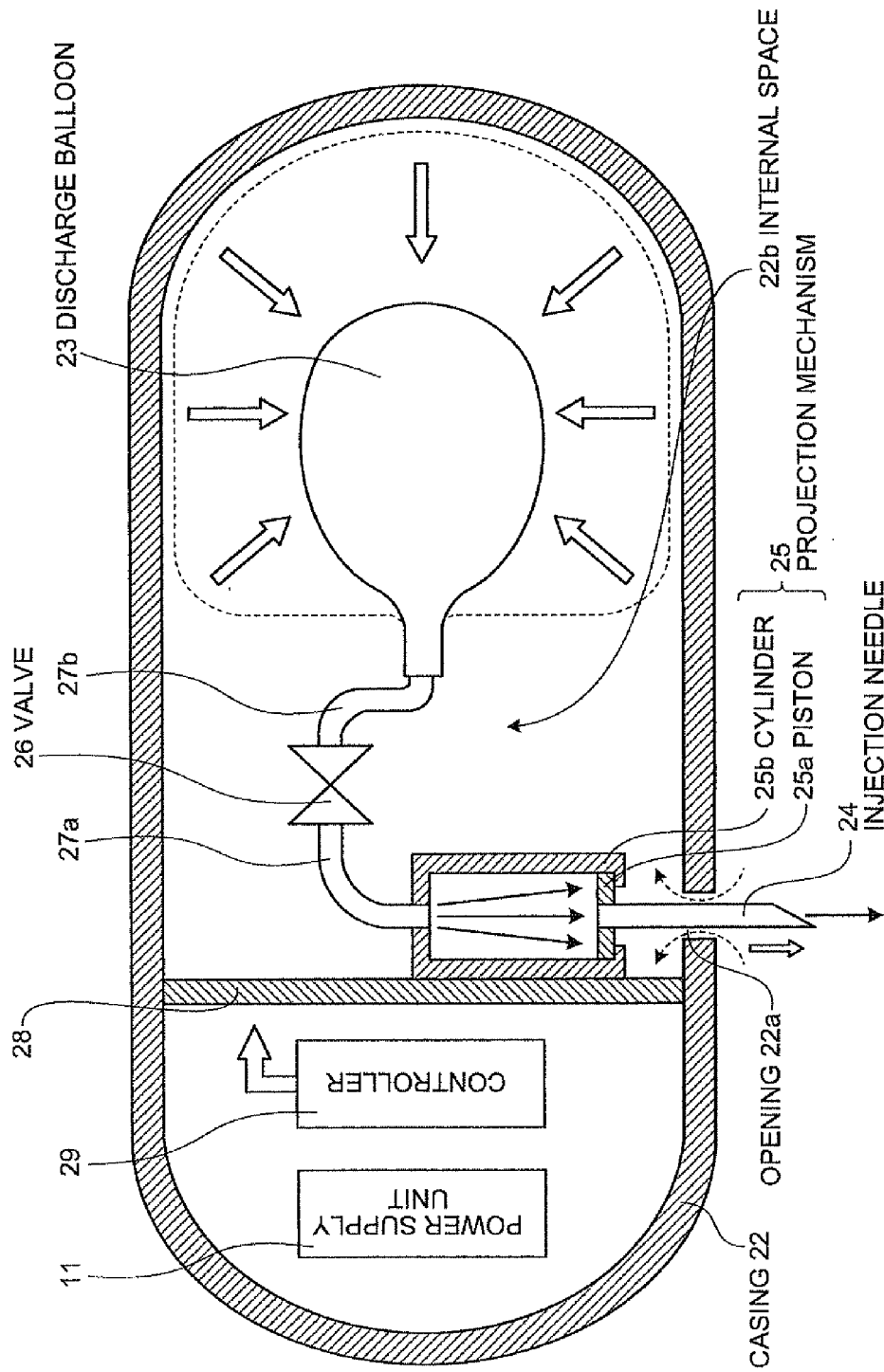
FIG. 9 is a schematic cross sectional view for explaining a fixing operation for casing by a discharge balloon and a projection operation for an injection needle by a projection mechanism.
Figure 10:
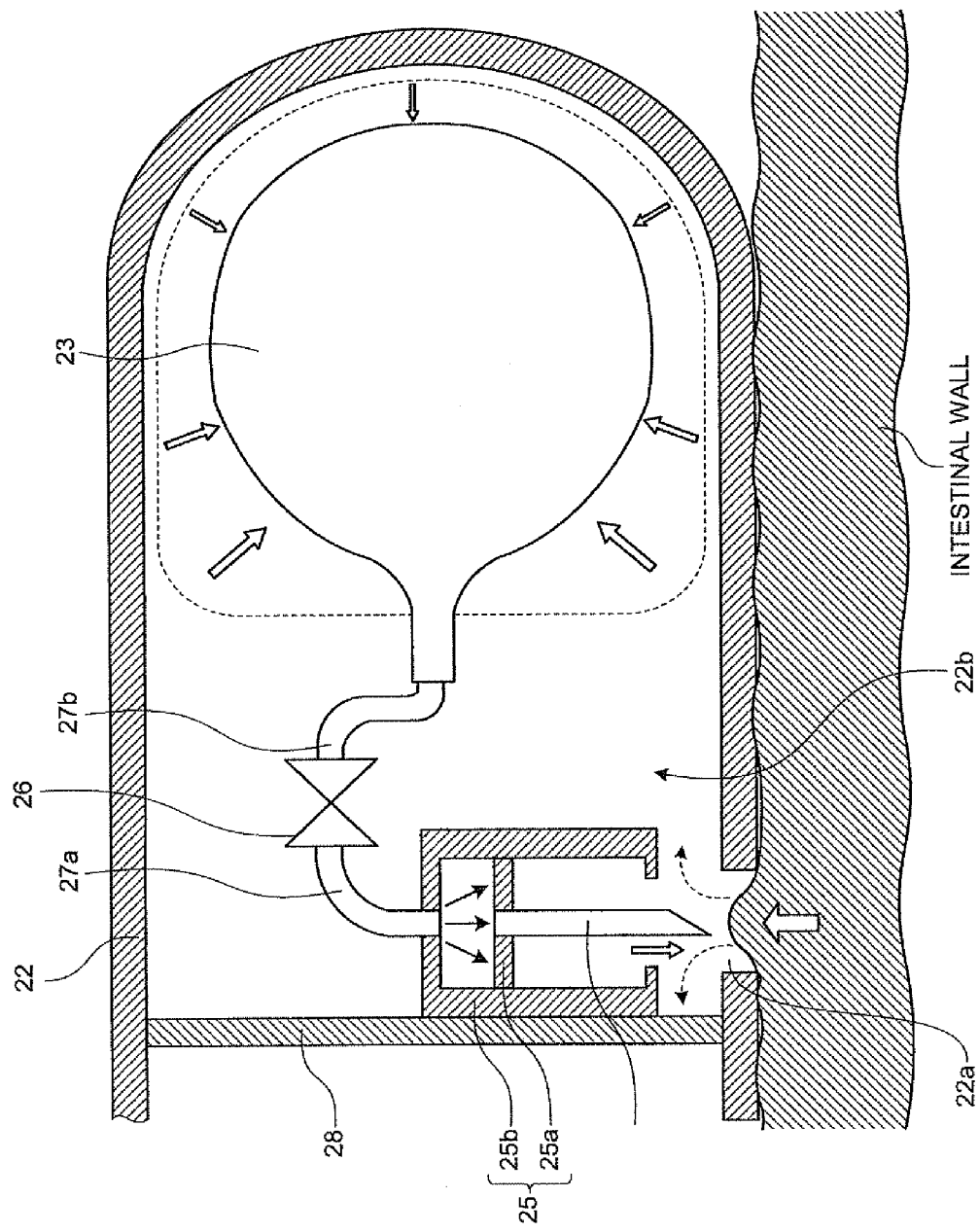
FIG. 10 is a schematic diagram showing a state wherein living tissue in a subject is sucked and the casing is fixed to a desired part in the subject.
Figure 11:
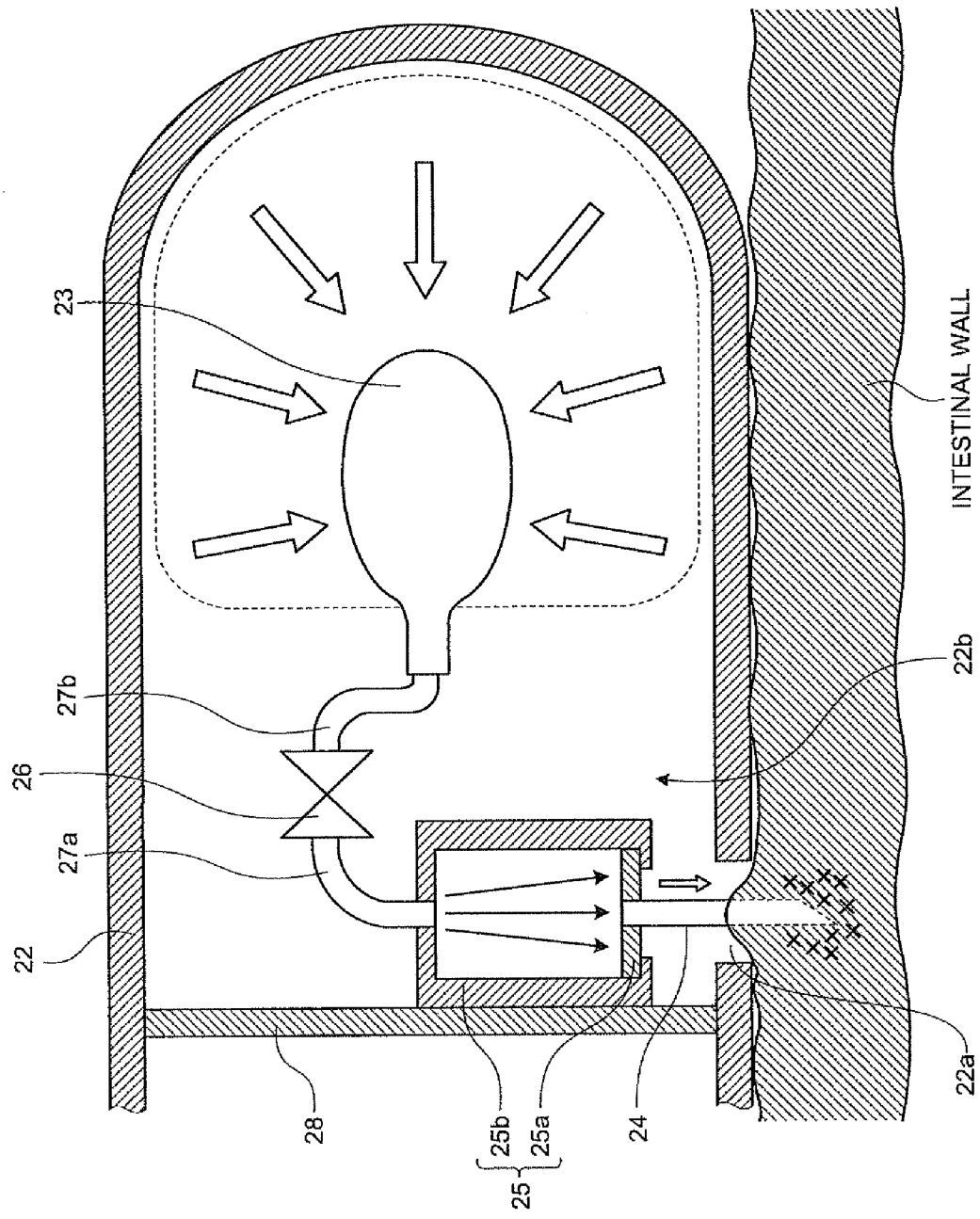
FIG. 11 is a schematic diagram exemplarily showing a state wherein an injection needle is stuck into a desired part in the subject.

Descriptions will now be made to an operation for fixing the casing 22 by the discharge balloon 23 and an operation for projecting the injection needle 24 by the projection mechanism 25. FIG. 9 is a schematic cross sectional view for explaining the operation for fixing the casing 22 by the discharge balloon 23 and the operation for projecting the injection needle 24 by the projection mechanism 25. FIG. 10 is a schematic diagram exemplarily showing a state wherein living tissue in the subject is sucked and the casing 22 is fixed in the desired part in the subject. FIG. 11 is a schematic diagram exemplarily showing that the injection needle 24 is stuck into the desired part in the subject. Descriptions will now be made to the operation of the discharge balloon 23 for fixing the casing 22 and the operation of the projection mechanism 25 for projecting the injection needle 24, with reference to FIG. 9 to FIG. 11.

The controller 29 controls the valve 26 to be open-driven, when the body-insertable apparatus 21 which has been introduced into the subject has reached a desired part in the subject. When the valve 26 is open-driven under the control of this controller 29, the discharge balloon 23 and the cylinder 25b are changed into a state where they are connected to each other through the valve 26 and the tubes 27a and 27b. In this case, the discharge balloon 23 begins the operation for discharging the medical agent by its own contraction force as a driving source.

The discharge balloon 23 discharges medical agent into the cylinder 25b through the valve 26 and the tubes 27a and 27b, and depressurizes the internal space 22b of the casing 22 by its own contraction effect so as to suck living tissue outside the casing 22 by the sucking force generated with this depressurization of the internal space 22b. In this case, as shown in FIG. 10, the balloon 23 discharges medical agent into the cylinder 25b, sucks the intestinal wall in the subject to the side of the internal space 22b through the opening 22a, and fixes the casing 22 in the desired part in the subject.

In cooperation with the operation for fixing the casing 22 by this discharge balloon 23, the projection mechanism 25 performs an operation for projecting the injection needle 24 to the outside of the casing 22. Specifically, the piston 25a slides in the cylinder 25b by the pressure of medical agent discharged from the discharge balloon 23 into the cylinder 25b so as to project the injection needle 24 through the opening 22a. In this state, the casing 22 is prevented from moving due to suction of the living tissue in the subject through the opening 22a. Thus, as shown in FIG. 11, the projection mechanism 25 can resist a reaction from the wall of the alimentary tract toward the injection needle 24 so as to easily control the injection needle 24 to be stuck into the desired part in the subject.

Accordingly, when the injection needle 24 punctures the desired part in the subject, the medical agent discharged by the discharge balloon 23 is injected to the desired part in the subject through the injection needle 24, etc. This state where the medical agent injected into the desired part remains until the contraction force of the discharge balloon 23 becomes zero, or until the valve 26 is close-driven under the control of the controller 29. As a result, a predetermined amount of medical agent can be injected to the desired part in the subject.

In this case, the discharge balloon 23 performs the above-described operation for discharging the medical agent and the operation for fixing the casing 22 by its potential contraction force as a driving source. The projection mechanism 25 performs the operation for projecting the injection needle 24 by the pressure of medical agent discharged by the contraction force of this discharge balloon 23 as a driving source. That is, the discharge balloon 23 and the projection mechanism 25 are driven by the contraction force of this discharge balloon 23 as one driving source, and further cooperate with each other.

In the second embodiment of this invention, the injection needle is fixed on the piston slidably provided inside the cylinder, and this piston slides by the pressure of medical agent so as to project the injection needle. However, this invention is not limited to this. The injection needle may be stored inside the casing by the elasticity of a spring which is provided between the opening end of the cylinder and the piston, upon completion of the process for injecting medical agent. In this case, the elasticity of the spring is low as compared to the medical agent discharge force for discharging medical agent (e.g. the contraction force of the discharge balloon).

In the second embodiment of this invention, the living tissue is sucked through the opening for projecting the injection needle. However, this invention is not limited to this. Aside from the opening (projection port) for projecting the injection needle, an opening (suction port) for sucking the living tissue in the subject may further be provided in the casing. In this case, the internal space of the casing having medical agent discharge means, such as the discharge balloon, etc. and the external of the casing are connected with each other through the suction port. Further, the internal space having this medical agent discharge means and the projection port are in a non-connection state, using a method for covering this projection port with the cylinder for forming the projection mechanism for the injection needle.

As described above, in the second embodiment of this invention, the medical agent is discharged by the medical agent discharge force (a physical force for discharging the medical agent) as one driving source so as to generate a sucking force. As a result, the wall of the alimentary tract in the subject is sucked by this sucking force so as to absorb the casing onto the wall of the alimentary tract in the subject, and also the injection needle is projected from the casing by the pressure of the medical agent. Thus, the casing can be fixed to the desired part in the subject, and the injection needle can be projected outside the casing, by the medical agent discharge force (e.g. the contraction force of the discharge balloon) as one driving source. This gives the same functional effect of the above-described first embodiment, and the projection mechanism for the injection needle can further be miniaturized, thus promoting miniaturization of the apparatus size of the body-insertable apparatus.

A third embodiment of this invention will now be described. A body-insertable apparatus according to the third embodiment has a function for projecting the injection needle and fixing the casing to a desired part in the subject, using driving source (i.e. electricity supplied by a power supply unit) as one driving force.

Figure 12:
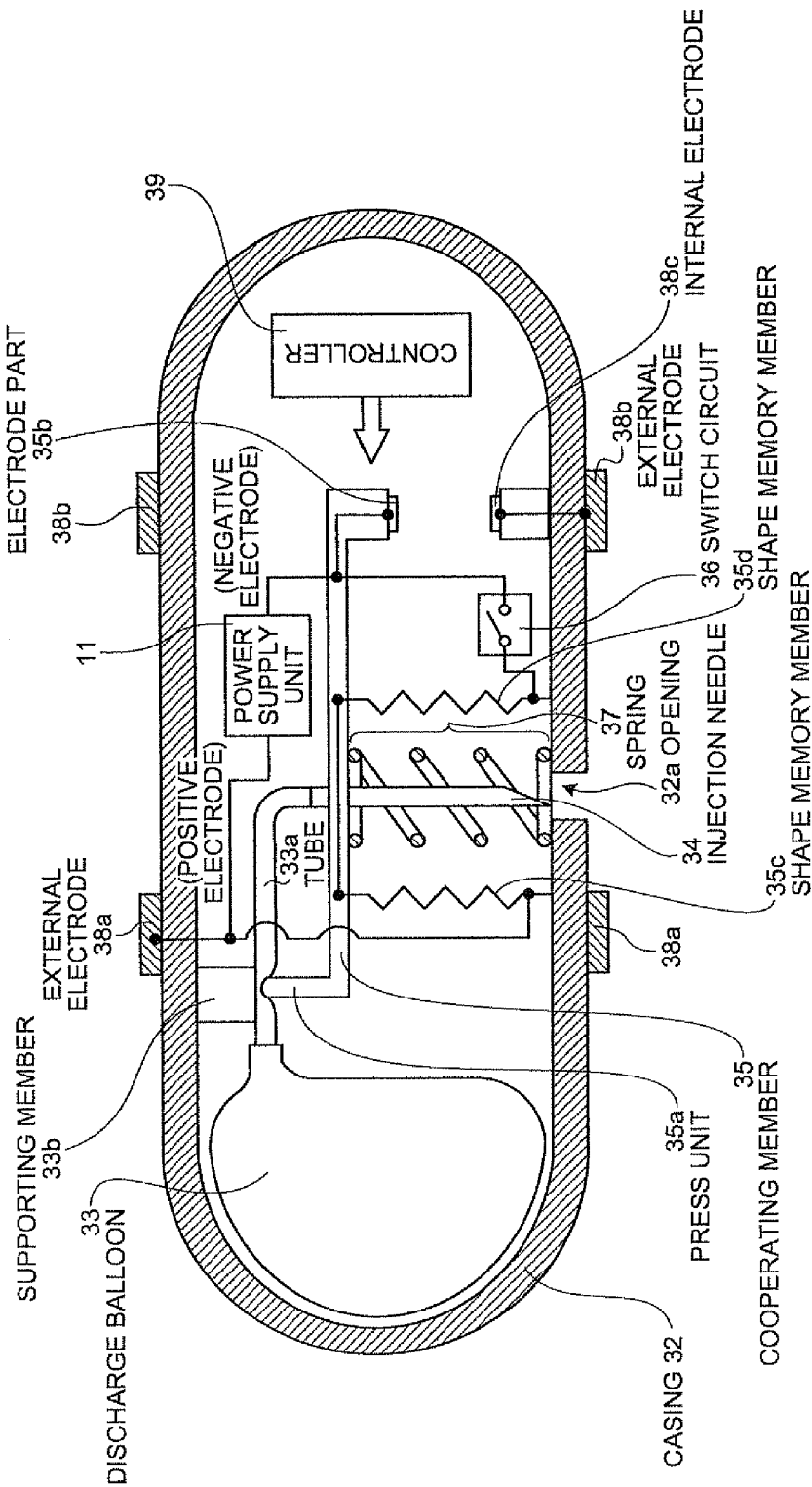
FIG. 12 is a schematic cross sectional view schematically showing a configuration example of a body-insertable apparatus as a third embodiment of this invention.

FIG. 12 is a schematic cross sectional view schematically showing a configuration example of the body-insertable apparatus as the third embodiment of this invention. As shown in FIG. 12, this body-insertable apparatus 31 includes a local injection mechanism for injecting medical agent inside capsulate-type casing 32 with such a size as to easily be introduced into a subject, and has fixing means for fixing the casing 32 to a desired part in the subject onto an external wall surface of this casing 32. Specifically, the body-insertable apparatus 31 has a pair of external electrodes 38a and 38b functioning as fixing means for the casing 32, on the external surface of this casing 32.

The body-insertable apparatus 31 has a discharge balloon 33, an injection needle 34, a cooperating member 35 and shape memory members 35c and 35d, inside this casing 32. The balloon 32 forms a storage chamber for storing medical agent and discharges the medical agent. The injection needle 34 is to inject the medical agent discharged by the discharge balloon 33 to a desired part in the subject. The cooperating member 35 is to support the injection needle 34 and to cooperatively carry out an operation for discharging medical agent, an operation for projecting the injection needle 34 and an operation for fixing the casing 32. The shape memory members 35c and 35d are to project this injection needle 34 from the casing 32. The body-insertable apparatus 31 has a tube 33a, a supporting member 33b and a spring 37. The tube 33a forms a circulation pipeline for medical agent circulating between the discharge balloon 33 and the injection needle 34. The supporting member 33b supports a part of the tube 33a. The spring 37 is to store the injection needle 34 projected from the casing 32 inside the casing 32. Further, the body-insertable apparatus 31 has a switch circuit 36, a controller 39, a power supply unit 11 and an internal electrode 38c. The switch circuit 36 switches ON/OFF a first electrical circuit including the shape memory members 35c and 35d. The controller 39 controls the driving of the switch circuit 36. The power supply unit 11 is to supply driving power to the shape memory members 35c and 35d, the external electrodes 38a and 38b and the controller 39. The internal electrode 38c forms one end terminal of a switch circuit for switching ON/OFF a second electrical circuit including the external electrodes 38a and 38b. The casing 32 includes an opening 32 for inserting the injection needle 34.

The discharge balloon 33 is to discharge medical agent to be injected to a desired part in the subject. Specifically, the discharge balloon 33 is realized with an elastic member, such as rubber, etc., expands upon injection of medical agent, and stores medical agent while maintaining this expansion state. Such a discharge balloon 3 applies pressure to medical agent by its contraction force (potential to it while maintaining medical agent) so as to discharge it, and circulates the medical agent to the pipeline of the injection needle 34 through the tube 33a.

One end of the tube 33a is connected to the discharge port of the discharge balloon 33, while the other end thereof is connected to the base end of the injection needle 34, thereby connecting between the discharge balloon 33 and the injection needle 34. In this case, the tube 33a forms a pipeline for circulating the medical agent discharged by the discharge balloon 33 to the line of the injection needle 34. A part of the tube 33a is mounted on the supporting member 33b. A connection state of this discharge balloon 33 and the injection needle 34 is adjusted by the effect of the cooperating member 35 corresponding to the part mounted on this supporting member 33b.

The injection needle 34 is to inject the medical agent discharged by the discharge balloon 33 to the desired part in the subject. Specifically, the injection needle 34 includes a line connecting an end side (pointed side) puncturing the subject and the base end side, the line of this injection needle 34 and the internal space of the discharge balloon 3 are connected to each other though the tube 33a, and the periphery of the base end of this injection needle 34 is fixed onto the cooperating member 35. Such an injection needle 34 operates in cooperation with the cooperating member 35 by the effect of the shape memory members 35c and 35d, as will be described later, and is projected from the casing 32 through the opening 32a.

The cooperating member 35 is to cooperatively carry out a projection operation for projecting the injection needle 34 from the casing 32, an operation of the discharge balloon 33 for discharging medical agent and an operation for fixing the casing 32 to a desired part in the subject by generating a potential between the external electrodes 38a and 38b. Specifically, the cooperating member 35 includes wiring for forming a part of the first electrical circuit including the shape memory members 35c and 35d, so as to move the injection needle 34 from the casing to a projection direction by the effect of the shape memory members 35c and 35d, as will be described later.

The cooperating member 35 includes a press unit 35a formed on its one end and for pressing a part of the tube 33a, and includes also an electrode part 35b formed on the other end and forming a switch circuit with the internal electrode 38c. The press unit 35a presses the above-described part of the tube 33a toward the supporting member 33b, in a state where the injection needle 34 is stored inside the casing 32, thereby interrupting the connection between the discharge balloon 33 and the injection needle 34 through this tube 33a. Such a press unit 35a moves in such a direction as to separate from the tube 33a along with movement of the cooperating member 35 toward the projection direction of the injection needle 34, thereby changing that the discharge balloon 33 and the injection needle 34 are in a connection state through the tube 33a. The electrode part 35b is electrically connected to the power supply unit 11 and the switch circuit 36. The electrode part 35b forms one end terminal of a switch circuit switching ON/OFF the second electrical circuit including the external electrodes 38a and 38b. Such an electrode part 35b is separated from the internal electrode 38c in a state where the injection needle 34 is stored inside the casing, and is electrically connected to the internal electrode 38c in a state where the injection needle 34 is projected from the casing 32.

The shape memory members 35c and 35d function as projection means for projecting the injection needle 34 from the casing 32 by moving the cooperating member 35. Specifically, the shape memory members 35c and 35d have a rod-like or coil-like structure (e.g. SMA coil), have predetermined shape memory properties, and are formed of a shape memory alloy having a predetermined electrical resistance value. One ends of such shape memory members 35c and 35d are fixed onto the casing 32, while the other ends thereof are fixed onto the cooperating member 35. The shape memory members 35c and 35d have such a sufficient length that the injection needle 34 can be stored inside the casing 32 and a part of the tube 33a is squeezed by the press unit 35a, under the same temperature condition as the temperature in the subject, for example. The shape memory members 35c and 35d change their shape under a temperature equal to or greater than a predetermined value (e.g. a sufficient high temperature as compared to the temperature inside the subject), and function for moving the cooperating member 35 in a direction approaching the opening 32a (i.e. the projection direction of the injection needle 34) and to project the injection needle 34 from the casing 32.

The switch circuit 36 is to switch ON/OFF the first electrical circuit including the above-described shape memory members 35c and 35d. Specifically, one end of the switch circuit 36 is connected to the shape memory member 35d, while the other end thereof is connected to the power supply unit 11. In this case, the above-described first electrical circuit includes the shape memory members 35c and 35d, the switch circuit 36 and the power supply unit 11, switches ON/OFF in accordance with the switch circuit 36, and is formed as an electrical circuit for driving the shape memory members 35c and 35d by electricity supplied by the power supply unit 11 as a driving source when it is in an ON state. Such a switch circuit 36 is controlled to be driven by the controller 39 so as to switch ON/OFF the first electrical circuit.

The spring 37 generates a pressing force to be applied to the cooperating member 35 in order to squeeze a part of the tube 33a using the press unit 35a and to store the injection needle 34 inside the casing 32. Specifically, one end of the spring 37 is fixed onto the cooperating member 35, while the other end thereof is fixed on to the casing 32, and its spring length is maintained in a state that it is shorter than a natural length. Thus arranged spring 37 can apply such a sufficient pressing force (elasticity) to the cooperating member 35 that a part of the tube 33a is squeezed by the press unit 35a and that the injection needle 34 is stored inside the casing 32.

The external electrodes 38a and 38b function as fixing means for fixing the casing 32 to the desired part in the subject by applying a current flowing to cause muscle contraction for the alimentary tract in the subject. Specifically, the external electrodes 38a and 38b are formed on the external wall surface of the casing 32, and are ring-like electrodes having a ring-like form around a central axis in a longitudinal direction of the casing 32. Such ring-like external electrodes 38a and 38b can usually be in contact with the wall of the alimentary tract in the subject, when the body-insertable apparatus 31 is introduced into the subject. In this case, the external electrode 38a is connected, for example, to the positive electrode of the power supply unit 11. The external electrode 38b is connected, for example, to the negative electrode of the power supply unit 11 through the electrode part 35b of the cooperating member 35 and the internal electrode 38c. A potential difference occurs between such external electrodes 38a and 38b, in a longitudinal direction of the casing 32 in accordance with a driving current supplied by the power supply unit 11, thus applying a driving current to the alimentary tract in the subject. That is, the external electrodes 38a and 38b cause muscle contraction in the alimentary tract in the subject by this driving current as a driving source, and press hard the casing 32 by this muscle contraction in the alimentary tract, thereby fixing the casing 32 to the desired part in the subject.

The internal electrode 38c forms one end terminal of the switch circuit switching ON/OFF the second electrical circuit including the above-described external electrodes 38a and 38b. Specifically, the internal electrode 38c is arranged in a position as the internal wall surface of the casing 32 and corresponding to the electrode part 35b of the cooperating member 35, and is electrically connected to the external electrode 38b. In this case, the above-described second electrical circuit includes the pair of external electrodes 38a and 38b, the electrode part 35b, the internal electrode 38c and the power supply unit 11, switches ON/OFF in accordance with the switch circuit formed of the electrode part 35b and the internal electrode 38c, and is formed as an electrical circuit for causing a potential difference between the external electrodes 38a and 38b based on driving power supplied by the power supply unit 11 in the ON state.

The controller 39 controls the switch driving for switching ON/OFF the first electrical circuit in accordance with the switch circuit 36, and controls the operation for projecting the injection needle 34, the operation for fixing the casing 32 and the operation for discharging medical agent through this control of the switch driving. Specifically, the controller 39 controls the driving of the switch circuit 36 to close the first electrical circuit (into an ON state), when the body-insertable apparatus 31 introduced into the subject has reached the desired part in the subject. In this case, the operation for projecting the injection needle 34 begins with the shape memory members 35c and 35d, the operation for discharging medical agent begins with the discharge balloon 33 in cooperation with this, and further the operation for fixing the casing 32 begins with the external electrodes 38a and 38b upon electrical connection of the electrode part 35b and the internal electrode 38c as a trigger. The controller 39 controls the driving of the switch circuit 36 to open the first electrical circuit (in to an OFF state). In this case, the injection needle 34 is stored inside the casing 32 by the effect of the spring 37, and the electrode part 35b and the internal electrode 38c are separated from each other so as to reset the fixed state of the casing 32. Further, a part of the tube 33a is squeezed by the press unit 35a so as to stop the operation for discharging medical agent.

In a configuration for setting a drive control timing of the switch circuit 36 in accordance with the controller 39, a timer mechanism may be included, or a radio receiving mechanism may be installed and an external control signal may be supplied to the controller 39.

Descriptions will now be made to a medical agent injection method according to the third embodiment of the present invention. According to the medical agent injection method for injecting medical agent into a desired part in a subject using the body-insertable apparatus 31 according to the third embodiment, along with approximately the same processing steps as above-described steps S101 to S104 shown in FIG. 3, it is introduced into a desired part in the subject (introduction step), the injection needle is projected toward this desired part (projection step), it is fixed to this desired part (fixing step), and medical agent is injected to this desired part (injection step). The projection step and the fixing step differ from those of the first embodiment, in the processing steps of this body-insertable apparatus 31.

Specifically, the body-insertable apparatus 31 projects the injection needle 34 from the casing 32 using the electricity of the power supply unit 11 as a driving source in this projection step. The body-insertable apparatus 31 applies a current flowing to the desired part in the subject through the external electrodes 38a and 38b so as to cause muscle contraction for this desired part using electricity of this power supply unit 11 as a driving source, thus fixing the casing 32 in this desired part by the effect of the muscle contraction.

Figure 13:
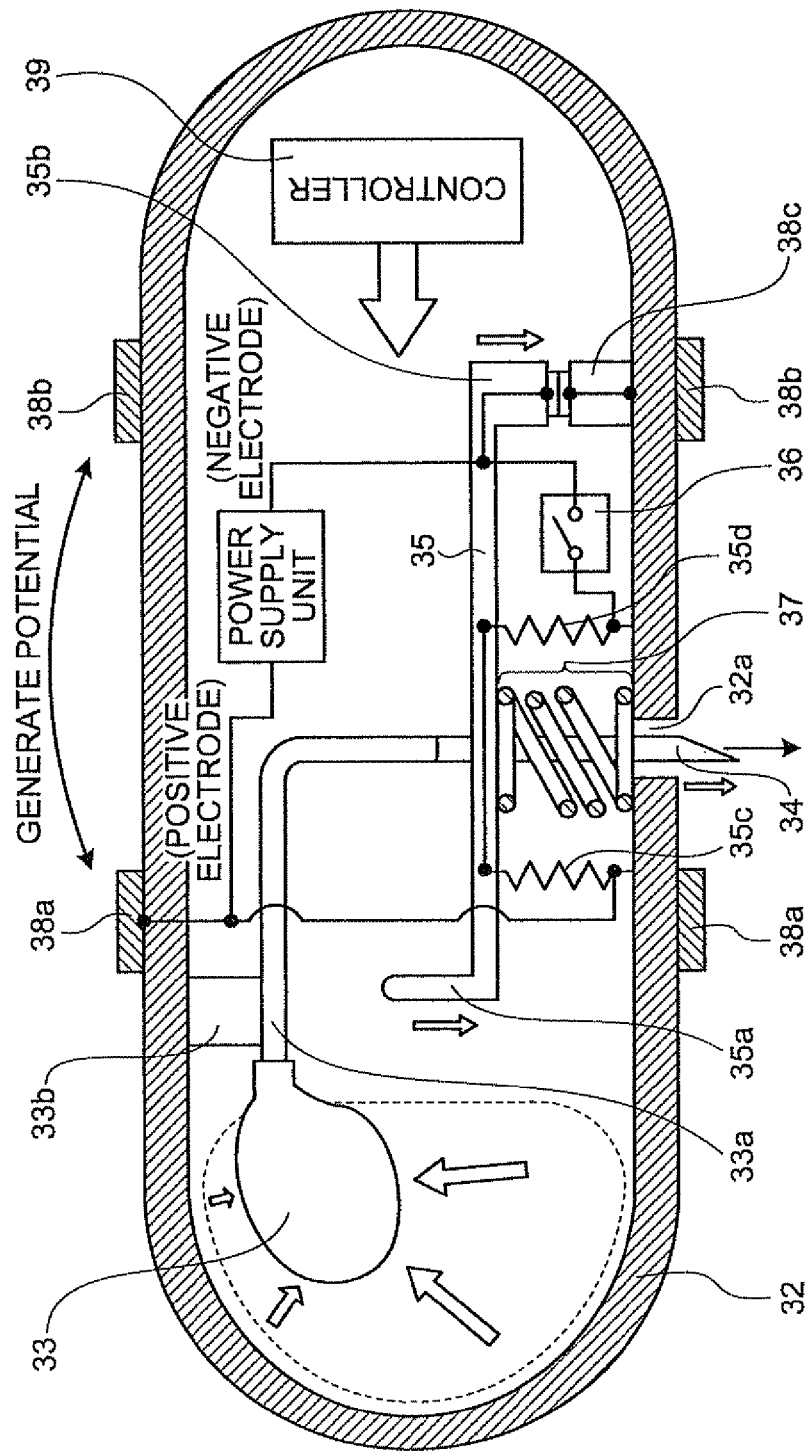
FIG. 13 is a schematic cross sectional view for explaining a projection operation for an injection needle by electric power as one driving source and a fixing operation for casing.
Figure 14:
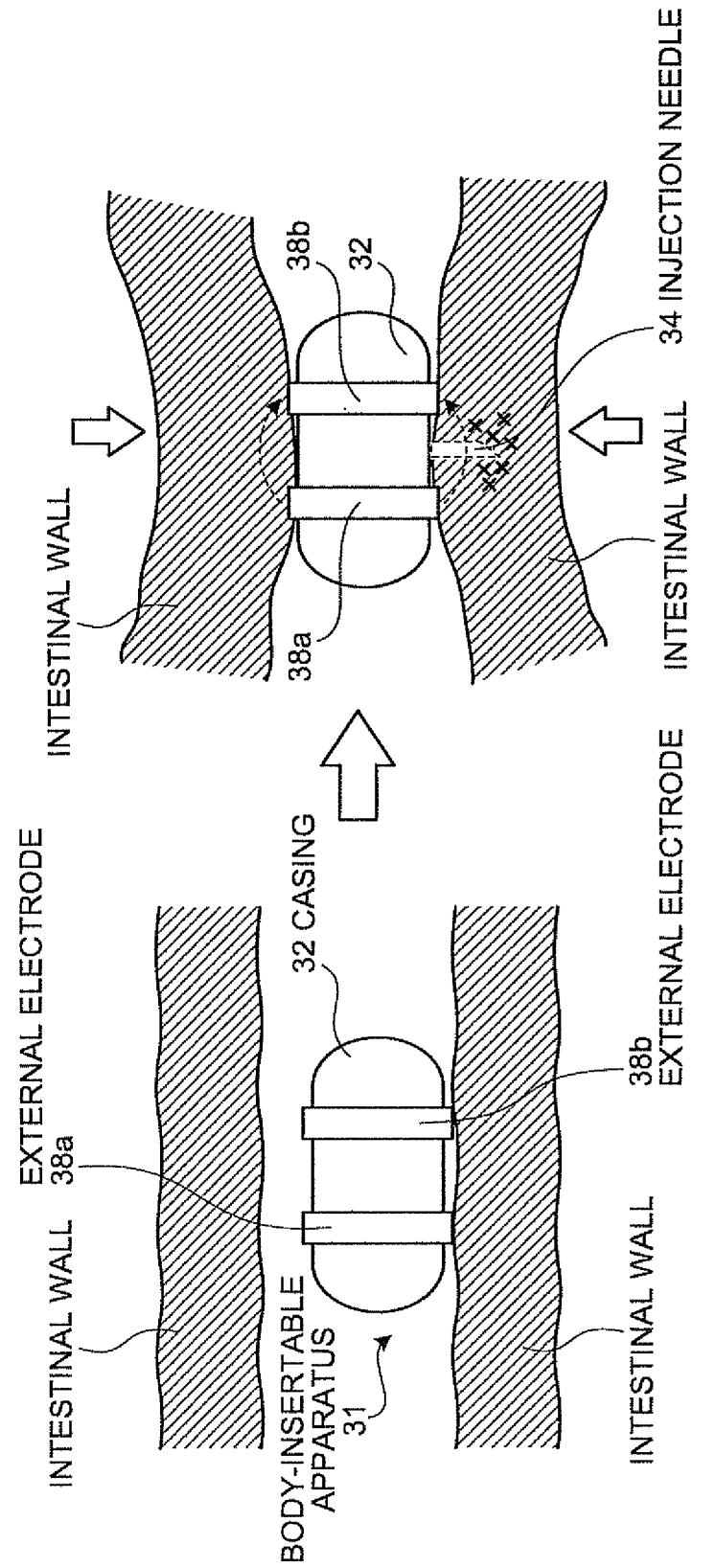
FIG. 14 is a schematic diagram exemplarily showing a state wherein the casing is fixed to a desired part in a subject by muscle contraction of alimentary tract.

Descriptions will now be made to the operation of the shape memory members 35c and 35d for projecting the injection needle 34 and the operation of the external electrodes 38a and 38b for fixing the casing 32. FIG. 13 is a schematic cross sectional view for explaining the operation for projecting the injection needle 34 and the operation for fixing the casing 32 using electricity as one driving source. FIG. 14 is a schematic diagram exemplarily showing a sate where the casing 32 is fixed in the desired part in the subject due to muscle contraction of the alimentary tract by causing a current flowing thereto. Descriptions will now be made to the operation of the shape memory members 35c and 35d for projecting the injection needle 34 and the operation of the external electrodes 38a and 38b for fixing the casing 32, with reference to FIG. 13 and FIG. 14.

The controller 39 controls the driving of the switch circuit 36, when the body-insertable apparatus 31 introduced into the subject has reached the desired part in the subject. When the switch circuit 36 is switched into an ON state under the control of this controller 39, the power supply unit 11 supplies the shape memory members 35c and 35d with a pulse current. The shape memory members 35c and 35d generate Joule heat by the pulse current supplied by this power supply unit 11 so as to increase its temperature to a predetermined value or higher. The temperature-increased shape memory members 35c and 35d cause a predetermined shape change (e.g. contraction change) so as to move the cooperating member 35 in a direction approaching the opening 32a of the casing 32. In this case, the shape memory members 35c and 35d project the injection needle 34 from the casing 32 together with the cooperating member 35, separate the press unit 35a from the tube 33a so as to reset the interruption state of the circulation pipeline for medical agent, and electrically connect the electrode part 35b and the internal electrode 38c. As described above, the shape memory members 35a and 35d perform the operation for projection of the injection needle 34.

In cooperation with the operation for projecting the injection needle 34 by the effect of the shape memory members 35c and 35d, the discharge balloon 33 performs the operation for discharging the medical agent using its own contraction force so as to make the medical agent circulate to the injection needle 34 through the tube 33a.

The power supply unit 11 supplies the external electrodes 38a and 38b with pulse driving power, when the electrode part 35b and the internal electrode 38c are electrically connected with each other along with the above-described operation for projecting the injection needle 34. In this case, a potential difference occurs between the external electrodes 38a and 38b based on the pulse driving power supplied by the power supply unit 11. For example, as shown in FIG. 14, a current flows to the alimentary tract of contact (small intestine or large intestine) in the subject so as to cause muscle contraction resulting in contracting the diameter of this alimentary tract. The external electrodes 38a and 38b press hard the casing 32 by thus generated muscle contraction of the alimentary tract so as to fix the casing 32 in the desired part in the subject.

Because the muscle contraction of the alimentary tract is thus caused, the casing 32 is prevented from moving. As a result, the injection needle 34 projected from the casing 32 by the effect of the shape memory members 35c and 35d can resist a reaction from the wall of the alimentary tract so as to easily puncture the desired part in the subject, as shown in FIG. 14. When the injection needle 34 punctures the desired part in the subject, the medical agent discharged by the discharge balloon 33 is injected to the desired part in the subject through the injection needle 34, etc. This state where the medical agent is injected to this desired part remains until the contraction force of the discharge balloon 33 becomes zero, or until the switch circuit 36 will be into an OFF state under the control of the controller 39. As a result, a predetermined amount of medical agent can be injected to the desired part in the subject.

After that, the controller 39 controls the driving of the switch circuit 36 to be into an OFF state, thereby to stop supplying the shape memory members 35c and 35d with driving power. As a result, the temperature of the shape memory members 35c and 35d decreases to a temperature lower than a predetermined value, thus losing a contraction force necessary for the operation for projecting the injection needle 34. In this case, the spring 37 applies a pressing force to the incorporating member 35 so as to move the incorporating member 35 in a direction separating from the opening 32a. Due to this effect of the spring 37, the electrode 35b and the internal electrode 38c separate from each other, and the injection needle 34 is stored inside the casing 32, and further the circulation pipeline having the tube 33a is interrupted by the press unit 35a. That is, the injection needle 34 is stored inside the casing 32, and the external electrodes 38a and 38b stop applying power to the alimentary tract, thereby resetting the fixed state of the casing 32 due to the muscle contraction of the alimentary tract and stopping the operation for discharging the medical agent.

Figure 15:
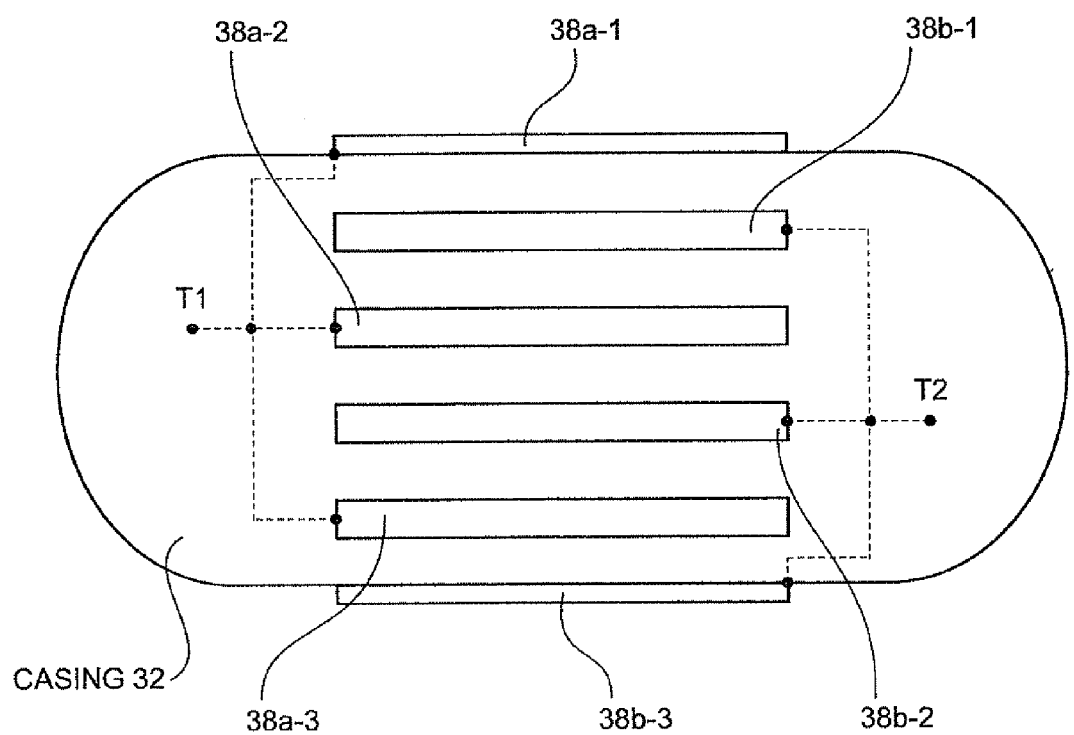
FIG. 15 is a schematic exterior view schematically showing a configuration example of the body-insertable apparatus as a modification of the third embodiment of this embodiment.

In the third embodiment of this invention, the ring-like external electrodes are provided on the external wall surface of the casing so as to cause muscle contraction of the alimentary tract by applying a current flowing thereto, and the potential difference is generated in a longitudinal direction of the casing. However, this invention is not limited to this. Comblike external electrodes including the positive and negative electrodes alternately in the circumferential direction of the casing may be provided on the external wall surface of the casing, and a potential difference may occur in the circumferential direction of the casing. As shown in FIG. 15, such comb-like external electrodes may include external electrodes 38a-1 to 38a-3 as elongated positive electrodes and external electrodes 38b-1 to 38b-3 as elongated negative electrodes that are alternately arranged in the circumferential direction of the casing 32. In this case, a terminal T1 electrically connected to the external electrodes 38a-1 to 38a-3 as the positive electrodes may be connected to the positive electrode of the power supply unit 11, while a terminal T2 electrically connected to the external electrodes 38b-1 to 38b-3 as the negative electrodes may be connected to the internal electrode 38c.

As described above, in the third embodiment of this invention, the injection needle is projected from the casing by the electricity supplied by the power supply unit, and this electricity is applied to the alimentary tract in the subject through the external electrode, thereby generating muscle contraction of the alimentary tract and pressing hard the casing by this muscle contraction of this alimentary tract. As a result, the casing can be fixed in the desired part in the subject by the electricity supplied by this power supply unit as one driving source, and the injection needle can be projected outside the casing. This gives the same functional effect as that of the above-described the first embodiment, and this realizes the body-insertable apparatus that can prevent movement of the casing without unintentionally puncturing the alimentary tract when puncturing the desired part in the subject.

Descriptions will now be made to a fourth embodiment of this invention. A body-insertable apparatus according to the fourth embodiment sets a magnetic force by an externally generated external magnetic field as one driving source, and functions for projecting an injection needle with this driving source and fixing the casing into a desired part in the subject.

Figure 16:
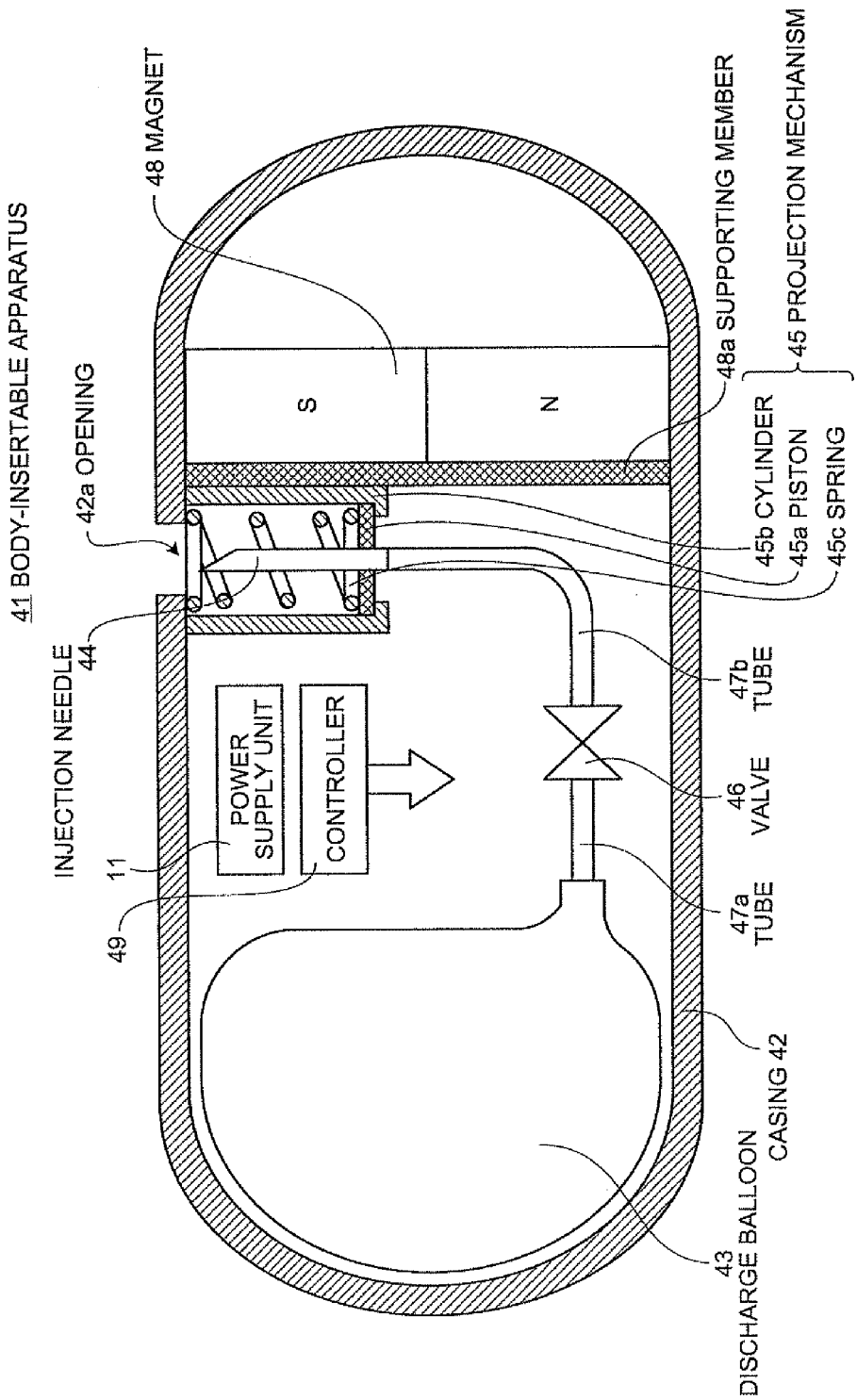
FIG. 16 is a schematic cross sectional view schematically showing a configuration example of a body-insertable apparatus as a fourth embodiment of this invention.

FIG. 16 is a schematic cross sectional view schematically showing a configuration example of the body-insertable apparatus as the fourth embodiment of this invention. As shown in FIG. 16, this body-insertable apparatus 41 includes a local injection mechanism for injecting medical agent, in capsule-type casing 42 with such a size as to easily be introduced into the subject. Specifically, the body-insertable apparatus 41 includes, inside this casing 42, a discharge balloon 43, an injection needle 44 and a projection mechanism 45. The discharge balloon 43 forms a storage chamber for storing medical agent and discharges the medical agent. The injection needle 44 injects the medical agent discharged by the discharge balloon 43 into a desired part in the subject. The projection mechanism 45 projects the injection needle 44 from the casing 42. The body-insertable apparatus 41 has a valve 46, a tube 47a and a tube 47b. The valve 46 is open/close-driven in order to start or stop the operation of the discharge balloon 43 for discharging medical agent. The tube 47a is to form a circulation pipeline for medical agent between the discharge balloon 43 and the valve 46. The tube 47b is to form a circulation pipeline for medical agent between the valve 46 and the projection mechanism 45. Further, the body-insertable apparatus 41 has a magnet 48, a supporting member 48a, a controller 49, and a power supply unit 11. The magnet 48 is to fix the casing 42 in the desired part in the subject. The supporting member 48a supports the magnet 48 in a predetermined position inside the casing 42. The controller 49 controls the open/close driving of the valve 46. The power supply unit 11 supplies the controller 49 with driving power. The casing 42 includes an opening 42a for inserting the injection needle 44.

The discharge balloon 43 is realized with an elastic member, such as rubber, etc., and expands upon injection of medical agent, and contains the medical agent while maintaining this expansion state. In this case, the discharge balloon 43 functions for discharging the contained medical agent, by its own contraction force (potential to it due to this expansion). Specifically, the discharge balloon 43 is connected to the valve 46 through the tube 47a, contracts when the valve 46 is open-driven, and applies pressure to medical agent with its own contraction force, so as to perform the operation for discharging the medical agent. The discharge balloon 43 stops to contract, when the valve 46 is close-driven, and stops the operation for discharging the medical agent.

The injection needle 44 is to inject the medical agent discharged by the discharge balloon 43 into the desired part in the subject. Specifically, the injection needle 44 includes a line for connecting an end side (pointed side) puncturing the subject and the base end side, and is connected to one end of the tube 47b. In this case, the line of the injection needle 44 is connected to the valve 46 through the tube 47b.

The projection mechanism 45 functions as projection means for projecting the injection needle 44 to the outside of the casing 42 with a magnetic force by an external magnetic field generated outside the casing 42 as a driving source. Specifically, the projection mechanism 45 is realized with a piston 45a on which the base end of the injection needle 44 is mounted, a cylinder 45b slidably storing this piston 45a and a spring 45c for storing the injection needle 44 projected through the opening 42a inside the casing 42.

The piston 45a is realized with a magnetic substance, such as iron or nickel, etc. Such a piston 45a is magnetized by an external magnetic field generated outside the casing 42, slides inside the cylinder 45b by a magnetic force of this external magnetic field as a driving source, and projects the injection needle 44 through the opening 42a.

The cylinder 45a is so fixed on the casing 42 that the path of the injection needle 44 fixed onto the slidably stored piston 45a corresponds to the opening 42a. Such a cylinder 45b so controls the sliding direction of the piston 45a that the injection needle 44 is inserted through the opening 42a so as to be projected from the casing 42.

The spring 45c is to store the injection needle 44 projected from the casing 42 inside the casing 42. Specifically, the spring 45c is provided between the periphery of the opening 42a of the casing 42 and the piston 45a, contracts as the piston 45a slides in a direction (projection direction) approaching the opening 42a by the magnetic force of the external magnetic field, and generates a pressing force (elasticity) for sliding the piston 45a in a direction (storage direction) separating from the opening 42a. Such a spring 45c makes this piston 45a slide in the storage direction so as to store the injection needle 44 inside the casing 42, when the magnetic force of the external magnetic field for attracting the piston 45a in this projection direction is increased to a predetermined value or lower.

The valve 46 is open/close-driven under the control of the controller 49, and adjusts the connection state of the discharge balloon 43 and the injection needle 44 through the tubes 47a and 47b. Specifically, the valve 46 is open-driven so as to make the connection state of the discharge balloon 43 and the injection needle 44, and begins the operation of the discharge balloon 43 for discharging medical agent. The valve 46 is close-driven so as to interrupt the connection of the discharge balloon 43 and the injection needle 44 and stop the operation for discharging medical agent by the discharge balloon 43.

The magnet 48 functions as fixing means for fixing the casing 42 into a desired part in the subject with the magnetic force of an external magnetic field as a driving source. Specifically, the magnet 48 is a permanent magnet for generating a magnetic field of a predetermined direction, and is fixed onto the supporting member 48a, thereby fixing the direction of this magnetic field toward the casing 42. In a state where an external magnetic field is generated in a predetermined direction outside the casing 42, such a magnet 48 settles the direction of the casing 42 correspondingly to the direction of this external magnetic field with the magnetic force of this external magnetic field as a driving source, and fixes the casing 42 into the desired part in the subject. In this case, the magnet 48 is attracted by the magnetic force of this external magnetic field or repeals it, thereby settling the direction of the casing 42 and pushing the periphery of the opening 42a of the casing 42 always to the wall of the alimentary tract in the subject.

The controller 49 is to control open/close driving of the valve 46. Specifically, the controller 49 controls the valve 46 to be open-driven so as to make the connection state between the discharge balloon 43 and the injection needle 44 and to start the operation for discharging the medical agent by the discharge balloon 43, when the body-insertable apparatus 41 introduced into the subject has reached the desired part in the subject. The controller 49 controls the valve 46 to be close-driven so as to make an interruption state of the connection between the discharge balloon 43 and the injection needle 44 and to stop the operation for discharging the medical agent by the discharge balloon 43. As described above, the controller 49 controls the operation for discharging the medical agent by the discharge balloon 43, through the drive controlling of this valve 46.

In a configuration for setting the timing of the controller 49 to control the driving of the valve 46, a timer mechanism may be included, for example, or a radio receiving mechanism may be installed and an external control signal may be supplied to the controller 49.

Descriptions will now be made to a medical agent injection method according to the fourth embodiment of the present invention. According to the medical agent injection method for injecting medical agent to the desired part in the subject using the body-insertable apparatus 41 according to the fourth embodiment, along with approximately the same processing steps as steps S201 to S203 shown in FIG. 8, it is introduced into the desired part in the subject (introduction step), fixed to the desired part so as to project the injection needle 34 (fixing/projection step), thereafter injecting medical agent to this desired part (injection step). In the processing steps of the body-insertable apparatus 41, the fixing/projection step differs from that of the above-described the second embodiment.

Specifically, the body-insertable apparatus 41 is fixed to the desired part in the subject by a magnetic force by the external magnetic field as a driving source, and the injection needle 34 is projected to this desired part, in this fixing/projection step. In this case, the body-insertable apparatus 41 magnetically adheres the opening 42a side of the casing 42 to the desired part in the subject so as to fix the casing 42 to this desired part, and operates the piston 45a as a magnetic substance to be attracted to the external magnetic field so as to project the injection needle 44 from the casing 42.

Figure 17:
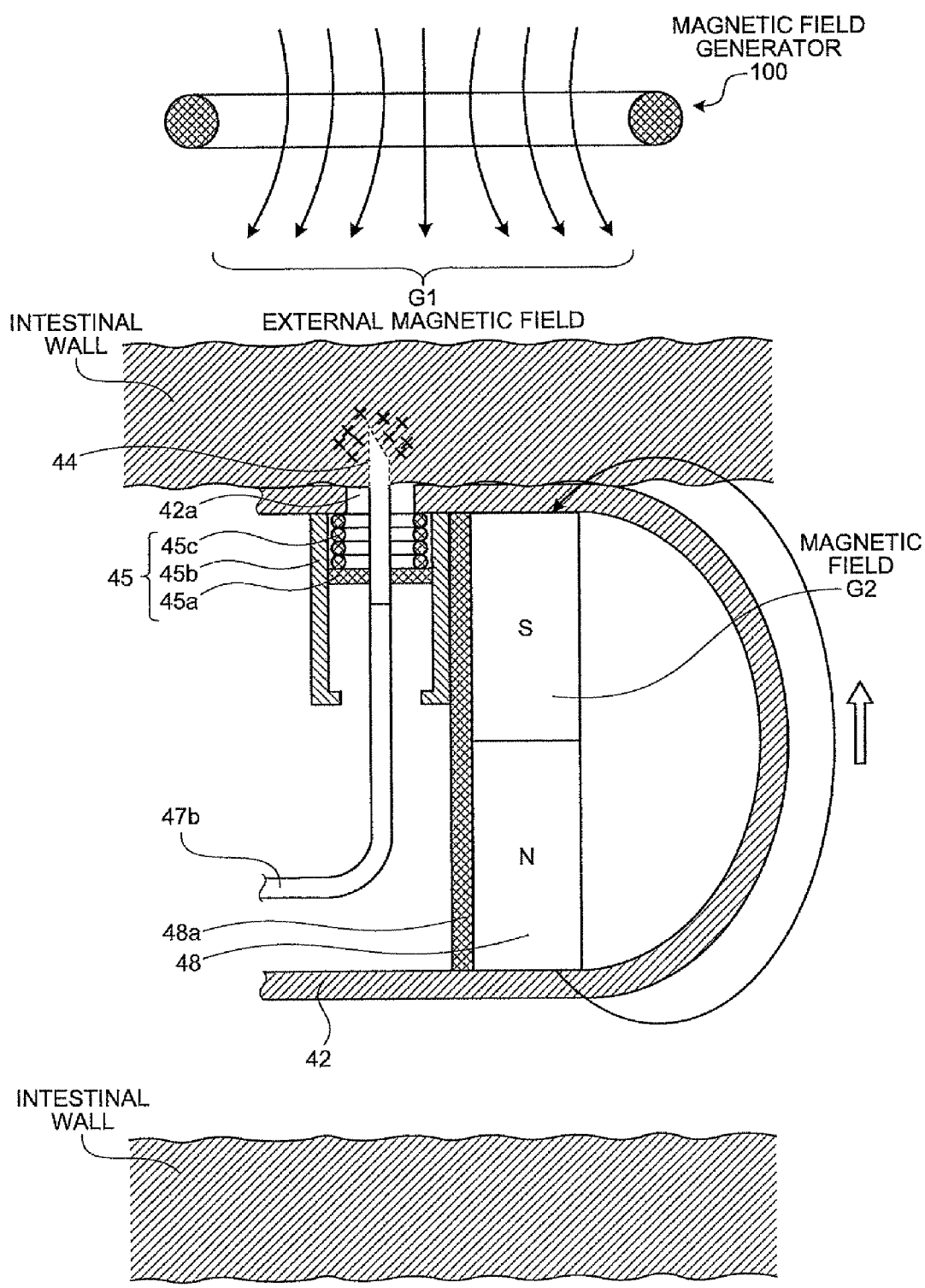
FIG. 17 is a schematic cross sectional view for explaining a fixing operation for casing by a magnetic force by a magnetic field as one driving source and a projection operation for an injection needle.

Descriptions will now be made to an operation for fixing the casing 42 by the magnet 48 and an operation for projecting the injection needle 44 by the projection mechanism 45. FIG. 17 is a schematic cross sectional view for explaining the operation for fixing the casing 42 and the operation for projecting the injection needle 44 with the magnetic force by the external magnetic field. Descriptions will now be made to the operation for fixing the casing 42 using the magnet 48 and the operation for projecting the injection needle 44 by the projection mechanism 45 with reference to FIG. 17.

A magnetic field generator 100, such as an electromagnet, etc., is provided outside the subject. This magnetic field generator 100 generates an external magnetic field G1 in a predetermined direction toward this body-insertable apparatus 41, when the body-insertable apparatus 41 introduced into the subject has reached the desired part in the subject (e.g. small intestine or large intestine). In this case, the external magnetic field G1 generates a sufficiently strong magnetic force to attract the magnet 48 through the wall of the alimentary tract, such as the intestinal wall in the subject, for example.

When such an external magnetic field G1 is generated outside the casing 42 through the wall of the alimentary tract in the subject, the magnet 48 settles the direction of the casing 42 correspondingly to the direction of the external magnetic field G1. Specifically, the magnet 48 always generates a magnetic field G2 fixed in a direction toward the casing 42, is attracted by the magnetic force of the external magnetic field G1, and changes the direction of the casing 42. As a result, the opening 42a of the casing 42 and the magnetic field generator 100 approximately face each other through the wall of the alimentary tract (e.g. intestinal wall, etc.) in the subject. As described above, as shown in FIG. 17, the magnet 48 pushes the periphery of the opening 42a of the casing 42 onto the intestinal wall in the subject using the magnetic force of the external magnetic field G1, and fixes the casing 42 to the desired part in the subject in such a state.

In cooperation with the fixing operation of the casing 42 by this magnet 48, the projection mechanism 45 projects the injection needle 44 from the casing 42 with the magnetic force by the external magnetic field G1 generated by the magnetic field generator 100 as a driving source. In this case, the piston 45a is magnetized by this external magnetic field G1, slides in the projection direction inside the cylinder 45a by the magnetic force of the external magnetic field G1, and projects the injection needle 44 from the casing 42 through the opening 42a.

In this case, the magnet 48 pushes the casing 42 onto the wall of the alimentary tract in the subject with the magnetic force by the external magnetic field G1 as a driving source, as described above. Thus, the casing 42 can be prevented from moving toward the desired part in the subject, and the projection mechanism 45 can control the injection needle 44 to easily be stuck into the desired part in the subject while resisting a reaction from the wall of the alimentary tract to the injection needle 44, in a state where the casing 42 is thus prevented from moving.

After that, the controller 49 controls the valve 46 to be open-driven, and makes the connection state between the discharge balloon 43 and the injection needle 44. In this case, the discharge balloon 43 performs the operation for discharging medical agent by its own contraction force, and makes medical agent circulate into the injection needle 44 through the tubes 47a, 47b and valve 46. The medical agent circulated to the injection needle 44 is injected to the desired part in the subject, as shown in FIG. 17. This state where the medical agent is injected into the desired part remains until the contraction force of the discharge balloon 43 will be zero, or the valve 46 is close-driven under the control of the controller 49.

As a result, a desired amount of medical agent can be injected to the desired part in the subject.

When medical agent is completely injected into the desired part in the subject, the magnetic field generator 100 stops a driving current for generating the external magnetic field G1 so as to cause the external magnetic field G1 to disappear. In this case, the state where the magnet 48 is pulled by the magnetic force of the above-described external magnetic field G1 is reset, and thus losing the pressing force of the casing 42 onto the wall of the alimentary tract in the subject. At the same timer the piston 45a loses the magnetic force. In this case, the spring 45c pushes the piston 45a in the storage direction of the injection needle 44 by the elasticity generated upon contraction along with the sliding of the above-described piston 45a in the projection direction, and stores the injection needle 44 in the casing 42. At this point, the state of the casing 42 where it is fixed to the desired part in the subject is reset, and the casing 42 is in such a state where it can move in the subject by peristaltic movement of the alimentary tract.

In the fourth embodiment of this invention, the external magnetic field G1 is generated using an electromagnet. However, this invention is not limited to this. The external magnetic field G1 may be generated using a permanent magnet. In this case, a permanent magnet is brought up to the body-insertable apparatus 41 having reached the desired part in the subject, externally from the subject, thereby generating a magnetic force sufficiently strong to fix the casing 42. This permanent magnet is moved in a direction separating from the body-insertable apparatus 41, thereby weakening the magnetic force of the external magnetic field toward the body-insertable apparatus 41 and resetting the fixed state of the casing 42.

In the fourth embodiment of this invention, the injection needle 44 is stored inside the casing 42 using the elasticity of the spring 45c. However, this invention is not limited to this. Without providing the spring 45c in the projection mechanism 45, an external magnetic field in an opposite direction to the external magnetic field G1 may be generated on the wall side of the alimentary tract facing the punctured position of the injection needle 44, the magnet 48 may be attracted by the magnetic force of the external magnetic field in the opposite direction so as to separate the casing 42 from the punctured position, and the piston 45a may slide in the storage direction of the injection needle 44 so as to store the injection needle 44 inside the casing 42.

Further, in the fourth embodiment of this invention, the piston 45a has been realized using a magnetic substance, such as iron or nickel, etc. However, this invention is not limited to this. The piston 45a may be realized using a permanent magnet. In this case, the piston 45a may be arranged inside the cylinder 45b in such a manner that the magnetic pole is in approximately the same direction as the magnet 48.

As described above, according to the configuration of the fourth embodiment of this invention, the magnet inside the casing is attracted by the magnetic force of the external magnetic field generated outside this casing, and the casing is pushed onto the wall of the alimentary tract inside the subject. In additions the piston with the injection needle mounted thereto is controlled to slide in the projection direction so as to project the injection needle from the casing. Thus, the casing can be fixed to the desired part in the subject and the injection needle can be projected to the outside of the casing. This gives the same effect as that of the above-described the first embodiment, and this realizes the body-insertable apparatus whose casing can be fixed to the desired part in the subject by the magnetic force.

Descriptions will now be made to a fifth embodiment of this invention. The body-insertable apparatus according to the fifth embodiment functions for pushing the casing onto the wall of the alimentary tract using a magnetic force by an externally generated rotating magnetic field as one driving source, projecting an injection needle, and fixing the casing to a desired part in the subject.

Figure 18:
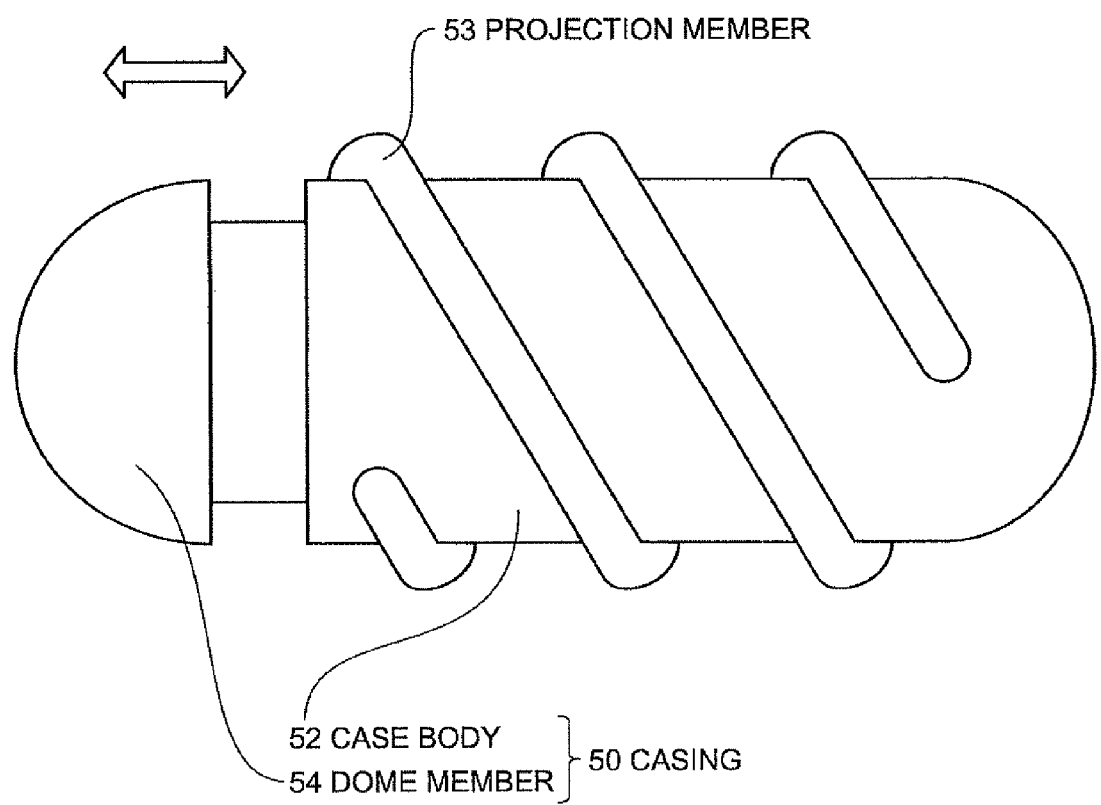
FIG. 18 is a schematic exterior view schematically showing a configuration example of a body-insertable apparatus as a fifth embodiment of this invention.
Figure 19:
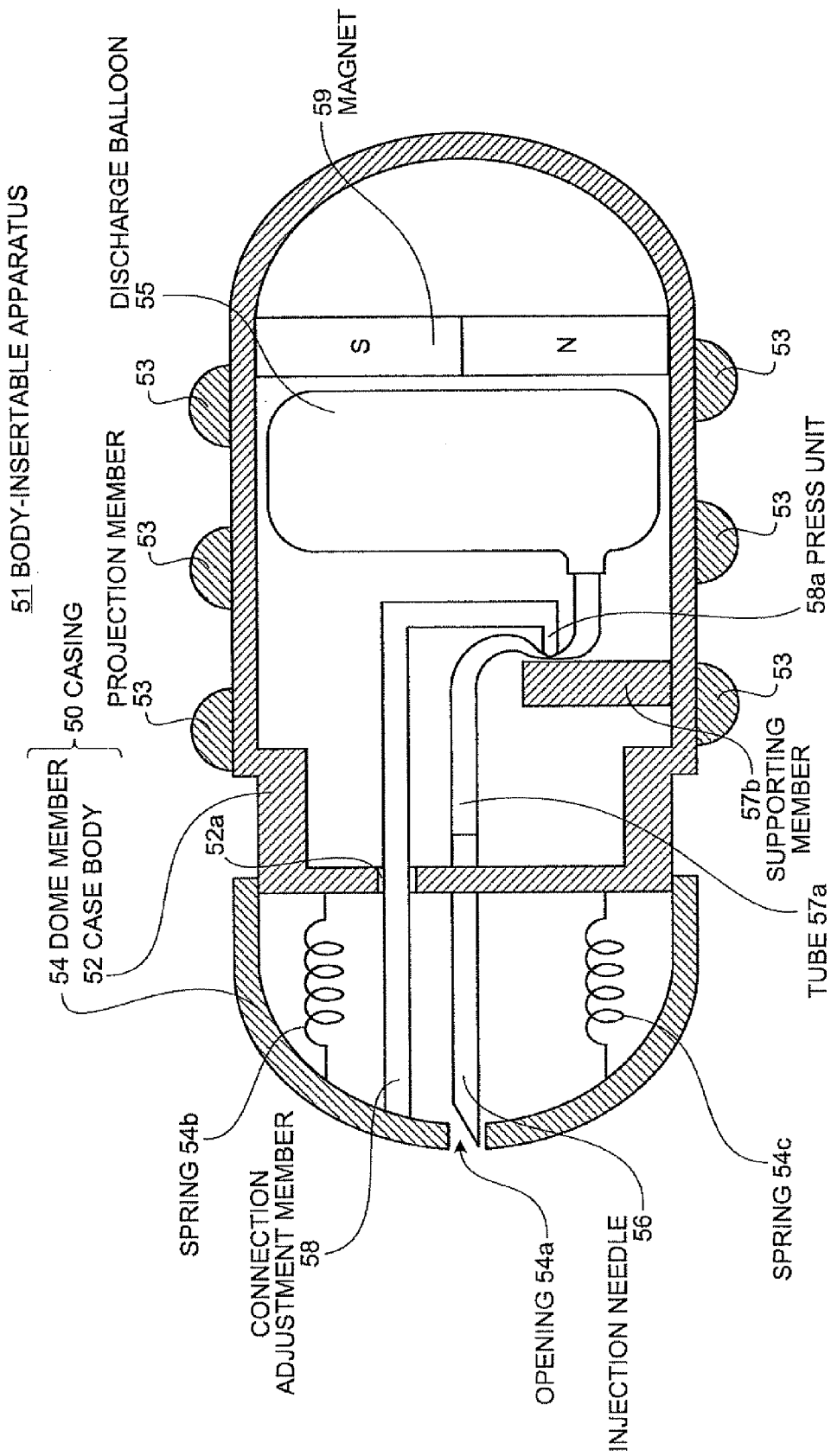
FIG. 19 is a schematic cross sectional view schematically showing a configuration example of a body-insertable apparatus as the fifth embodiment of this invention.

FIG. 18 is a schematic exterior view schematically showing a configuration example of the body-insertable apparatus as the fifth embodiment of this invention. FIG. 19 is a schematic cross sectional view schematically showing a configuration example of the body-insertable apparatus as the fifth embodiment of this invention. As shown in FIG. 18 and FIG. 19, the body-insertable apparatus 51 has a local injection mechanism for injecting medical agent inside casing 50, and has fixing means for pushing and fixing the casing 50 onto a desired part in the subject on the external wall surface of the casing 50.

The casing 50 is a movable terminal one end of which slides in a longitudinal direction, and is capsule-type casing with such a size as to easily be introduced into a subject. Specifically, the casing 50 has a dome member 54 for forming such a movable terminal and a case body 52 on one end of which the dome member 54 is slidably mounted. This dome member 54 is a dome-like member having an opening 54a for taking in and out an injection needle as will be described later, and slides in a longitudinal direction of the casing 52 so as to function as projection means for projecting the injection needle.

The casing 50 has a helical projection member 53 on the external wall surface of the casing body 52. The projection member 53 as a helical projection member functions as fixing means for pushing and fixing the casing 50 onto the desired part in the subject. Such a projection member 53 is provided on the case body 52 in a state of forming a helical around the central axis (i.e. cylindrical axis) in a longitudinal direction of the casing 50. A helical projection member may be formed from an indented unit (not illustrated) formed on the external surface of the casing 50, in place of the projection member 53.

The body-insertable apparatus 51 has, inside the casing 50, a discharge balloon 55, an injection needle 56, a tube 57a, a supporting member 57b and a connection adjustment member 58. The balloon 55 forms a storage chamber for storing medical agent and discharges the medical agent. The injection needle 56 injects the medical agent discharged by the discharge balloon 55 into a desired part in the subject. The tube 57a forms a circulation pipeline for medical agent circulating between the discharge balloon 55 and the injection needle 56. The supporting member 57b supports a part of the tube 57a. The connection adjustment member 58 adjusts the connection state of the discharge balloon 55 and the injection needle 56. The body-insertable apparatus 51 has springs 54b and 54c for slidably connecting the case body 52 and the dome member 54, and a magnet 59 for rotating the casing 50 by the magnetic force of an external rotating magnetic field.

The springs 54b and 54c slidably connect the case body 52 and the dome member 54, and control the dome member 54 slid in a longitudinal direction toward the case body 52 to return to its original position before sliding. Specifically, one ends of the springs 54b and 54c are fixed to the case body 52, while the other ends thereof are fixed to the dome member 54, and the spring length is maintained in a state where it is shorter than a natural length. Thus arranged springs 54b and 54c always generate elasticity (pressing force) in a direction separating the dome member 54 from the case body 52. In this case, unless a pressing force equal to or greater than this elasticity is applied in the longitudinal direction to the dome member 54, the springs 54b and 54c push back the dome member 54 to its original position before sliding and maintain the initial state (i.e. a state where the injection needle 56 is stored inside the dome member 54). When a pressing force equal to or greater than this elasticity is applied to the dome member 54 in the longitudinal direction, the springs 54b and 54c contract so as to slide the dome member 54 toward the case 52.

The discharge balloon 55 is realized with an elastic member, such as rubber, etc., and is arranged inside the case body 52. Specifically, the discharge balloon 55 expands upon injection of medical agent, and contains medical agent while maintaining this expansion state. In this case, the discharge balloon 55 functions for discharging the contained medical agent by its contraction force (potential to it doe to this expansion). This discharge balloon 55 contracts when it is connected to the injection needle 56 through the tube 57a, and performs an operation for discharging the medical agent upon application of pressure to the medical agent by its own contraction force. The discharge balloon 55 stops to contract when the circulation pipeline of the tube 57a is interrupted so as to stop the operation for discharging the medical agent.

The injection needle 56 is to inject the medical agent discharged by the discharge balloon 55 to a desired part in the subject. Specifically, the injection needle 56 includes a line connecting an end side (pointed side) puncturing the subject and the base end side, and is fixed to an end of the case body 52 (the end on which the dome member 54 is slidably provided). In this case, the injection needle 56 is covered by the dome member 54 in its original position before sliding, and is so arranged as to be inserted into the opening 54a when the dome member 54 slides in a longitudinal direction.

The tube 57a is to circulate the medical agent discharged by the discharge balloon 55 through the injection needle 56. Specifically, one end of the tube 57a is connected to the discharge port of the balloon 55 while the other end thereof is connected to the injection needle 56, and the internal space of the discharge balloon 55 and the line of the injection needle 56 are connected with each other. A part of the tube 57a is supported by the supporting member 57b. The supporting member 57b is fixed in a predetermined position inside the case body 52.

The connection adjustment member 58 is to adjust the connection state between the discharge balloon 55 and the injection needle 56 through the tube 57a. Specifically, one end of the connection adjustment member 58 includes a press unit 58a which is formed to press a part of the tube 57a, and the other end thereof is fixed on the internal wall of the dome member 54. In this case, the body part of the connection adjustment member 58 (i.e. the rod-like part between the press unit 58a and the installation unit toward the dome member 54) is inserted to the opening unit 52a formed at the end of the case body 52. Such a connection adjustment member 58 presses the press unit 58a onto a part of the tube 57a on the supporting member 57b, and interrupts the connection between the discharge balloon 55 and the injection needle 56 through this tube 57a, in a state where the dome member 54 is pressed into its original position before sliding. The connection adjustment member 58 makes the dome member 54 slide toward the case body 52 and separates the press unit 58a from a part of the tube 57a, and makes a connection state between the discharge balloon 55 and the injection needle 56 through the tube 57a.

The magnet 59 is to rotatably drive the casing 50 by a magnetic force of a rotating magnetic field generated outside the casing 50 using an external magnetic field generator (not illustrated). Specifically, the magnet 59 is a permanent magnet generating a magnetic field in a predetermined direction, and is fixed onto the case body 52. As a result, the direction of the magnetic field of the magnet 59 is fixed onto the case body 52. Such a magnet 59 rotatably drives the case body 52 correspondingly to the rotating direction of this rotating magnetic field, using a magnetic force by a rotating magnetic field as a driving source, in a state where the rotating magnetic field in a predetermined rotating direction is generated outside the casing 50. In this case, the magnet 59 rotatably drives the case body 52 around the cylindrical axis of the casing 50, and causes the projection member 53 rotating together with this case body 52 to generate a thrust force. This thrust force is to move the casing 50 along the alimentary tract in the subject, and will be a pressing force for pressing the casing 50 against a desired part in the subject, for example.

Figure 20:
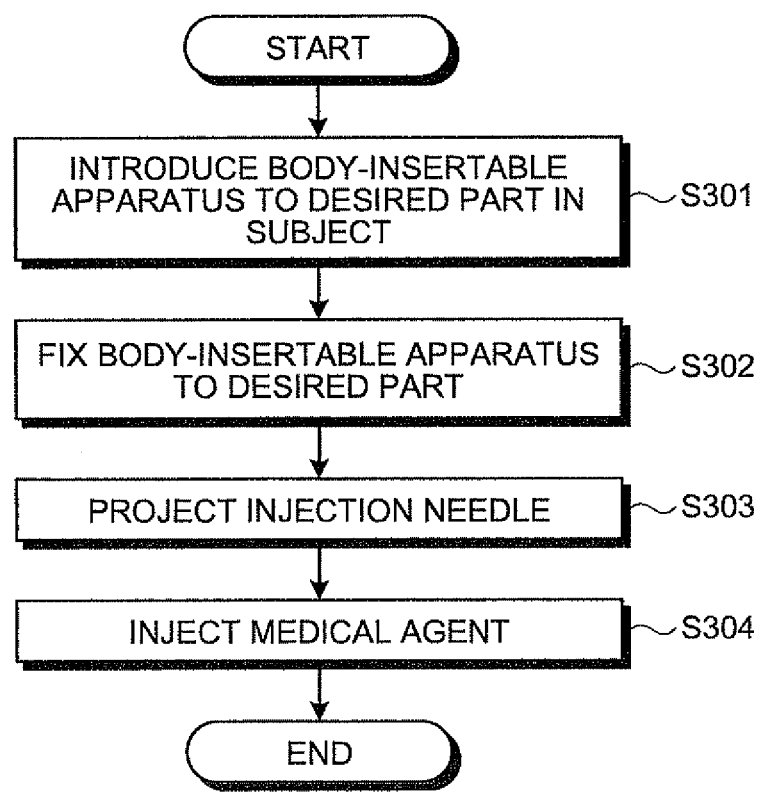
FIG. 20 is a flowchart for explaining a medical agent injection method according to the fifth embodiment of the present invention.

Descriptions will now be made to a medical agent injection method according to the fifth embodiment of the present invention. FIG. 20 is a flowchart for explaining the medical agent injection method according to the fifth embodiment of the present invention. Descriptions will hereinafter be made to the medical agent injection method, by way of example with reference to the case where medical agent is injected into a desired part in the subject using the body-insertable apparatus 51 according to the fifth embodiment.

As shown in FIG. 20, the body-insertable apparatus 51 is introduced into the desired part in the subject, such as a patient, etc. (Step S301). In this case, the body-insertable apparatus 51 is introduced from the mouth of the subject into the body, moves inside internal organs by an external rotating magnetic field or by peristaltic movement, and arrives the desired part (diseased part, etc.) in this subject.

The body-insertable apparatus 51 having reached the desired part in the subject through this step S301 (introduction step) is approximately fixed in a relative position with respect to the desired part in the subject (Step S302). In this step S302 (fixing state), the body-insertable apparatus 51 is rotatably driven using a magnetic force by an external rotating magnetic field as a driving source, presses the casing 50 against the desired part in the subject, and is fixed in the relative position with respect to this desired part.

The body-insertable apparatus 51 projects the injection needle 56 from the casing using the magnetic force by this external rotating magnetic field as a driving source (Step S303). In this step S303 (projection step), the body-insertable apparatus 51 further presses the dome member 54 against the desired part in the subject using the magnetic force by this external rotating magnetic field as a driving source, thereby causing the dome member 54 to slide so as to project the injection needle 56.

After that, the body-insertable apparatus 51 injects medical agent into the desired part in the subject through this injection needle 56, in a state where the injection needle 56 pierces and/or pushes the desired part in the subject (Step S304). In this step S304, the body-insertable apparatus 51 injects the medical agent inside the discharge balloon 55 to the desired part in the subject through the injection needle 56. As described above, the body-insertable apparatus 51 attains a medical agent injection process for the desired part in the subject.

Figure 21:
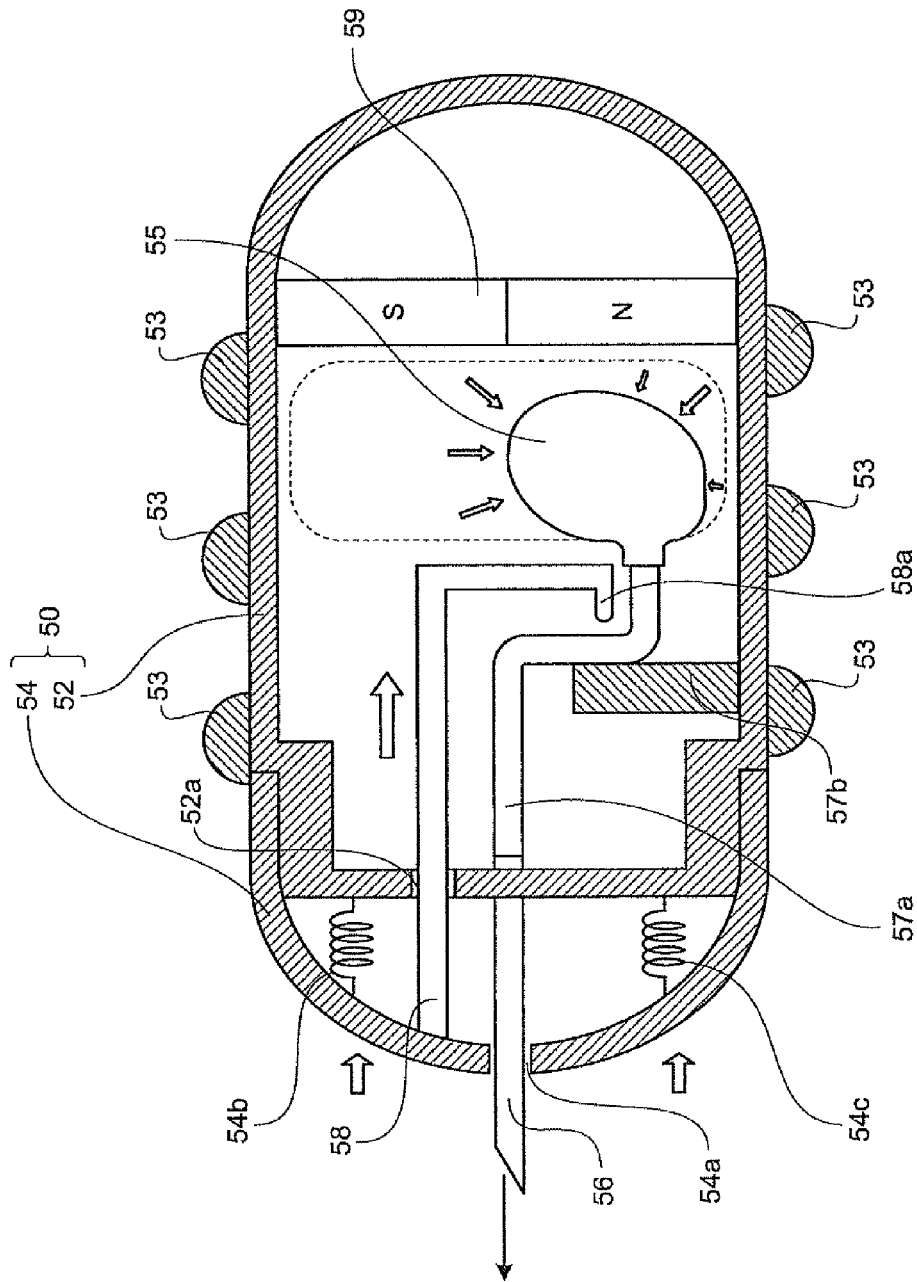
FIG. 21 is a schematic cross sectional view for explaining a projection operation for an injection needle by sliding of a dome member.
Figure 22:
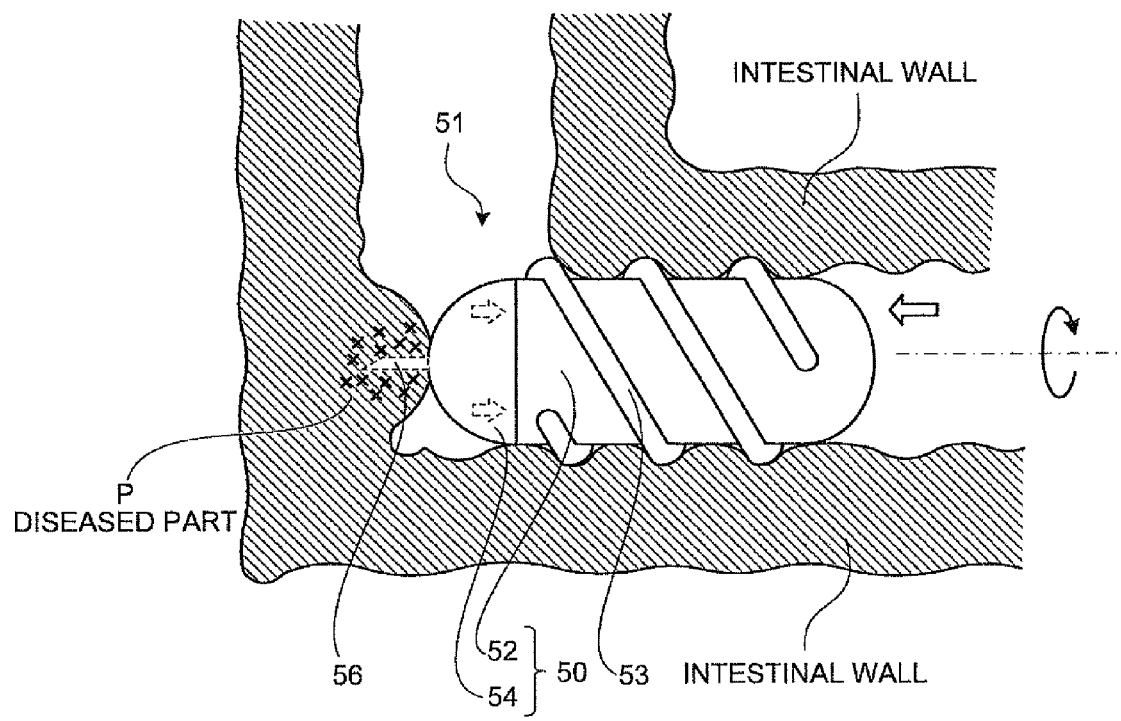
FIG. 22 is a schematic diagram for explaining a fixing operation for casing by a helical projection member.

Descriptions will now be made to an operation for projecting the injection needle 56 by sliding the dome member 54 and an operation for fixing the casing 50 by the helical projection member 53. FIG. 21 is a schematic cross sectional view for explaining the operation for projecting the injection needle 56 by sliding the dome member 54. FIG. 22 is a schematic cross sectional view for explaining the operation for fixing the casing 50 by the helical projection member 53.

Descriptions will now be made to the operation for fixing the casing 50 and the operation for projecting the injection needle 56, using the magnetic force by the external rotating magnetic field as one driving source, by reference to FIG. 21 and FIG. 22.

A predetermined rotating magnetic field is generated by a magnetic field generator (not illustrated) arranged outside the subject, for the body-insertable apparatus 51 introduced into the subject. As shown, for example, in FIG. 22, in a state where the external rotating magnetic field is generated, the body-insertable apparatus 51 rotatably drives the casing 50 around the cylindrical axis and moves along the alimentary tract in the subject (small intestine or large intestine). Specifically, the magnet 59 rotatably drives the case body 52 around the cylindrical axis of the casing 50, using the magnetic force by the external rotating magnetic field as a driving source. In this case, the projection member 53 is engaged with unevenness of the wall of the alimentary tract in the subject, is rotatably driven with this case body 52, and moves the casing 50 toward the desired part in the subject (e.g. diseased part P).

The projection member 53 continues to rotatably be driven with the above-described case body 52, moves the casing 50 toward the diseased part P, and presses the dome member 54 against the diseased part P. In this case, the dome member 54 slides in a longitudinal direction of the casing 50 (i.e. a direction toward the case body 52) using a pressing force by the rotation driving of this projection member 53, and projects the injection needle 56 through the opening 54a, as shown in FIG. 21, for example.

The casing 50 is pressed against the diseased part P using the pressing force generated by the rotation driving of the projection member 53, thereby preventing movement of the casing 50 toward the diseased part P. As a result, the injection needle 56 projected by the sliding of this dome member 54 resists a reaction from the diseased part P to the injection needle 56 so as to easily puncture the diseased part P.

In cooperation with this operation for projecting the injection needle 56, the connection adjustment member 58 separates the press unit 58a from a part of the tube 57a so as to reset the interruption state of the circulation pipeline of the tube 57a. In this case, the discharge balloon 55 is connected to the injection needle 56 through the tube 57a, and performs an operation for discharging medical agent by its contraction force. The medical agent discharged by this discharge balloon 55 is injected to the diseased part through the tube 57a and the injection needle 56.

This state where the medical agent is injected to the desired part remains until the contraction force of the discharge balloon 55 will be zero, or the dome member 54 returns into its original position before sliding so that the connection adjustment member 58 interrupts the circulation pipeline of the tube 57a. As a result, a desired amount of medical agent can be injected to the desired part in the subject.

After that, a rotating magnetic field is generated in a reverse direction to the body-insertable apparatus 51 by an external magnetic field generator (not illustrated). In this case, the magnet 59 is to rotatably drive the case body 52 in a reverse direction around the cylindrical axis of the casing 50, using the magnetic force by this rotating magnetic filed in the reverse direction. The projection member 53 is rotatably driven in a reverse direction with this casing body 52 so as to move the casing 50 in a direction separating from the diseased part P. Along with the movement of this casing 50, the springs 54b and 54c push back the dome member 54 into its original position before sliding. The dome member 54 returns into its original position so as to store the injection needle 56 therein.

At this point, the casing 50 is in a state where it can move in the subject by peristaltic movement of the alimentary tract.

When the casing 50 is pushed against the diseased part P, the magnet 59 rotatably drives the case body 52 using a magnetic force by the external rotating magnetic field as a driving source, and the projection member 53 is rotatably driven together with this case body 52 so as to press the casing 50 toward the desired part in the subject. That is, the projection member 53 is rotatably driven using the magnetic force by this rotating magnetic field as a driving source, presses and fixes the casing 50 onto the desired part in the subject. The dome member 54 slides along with the rotating driving of this projection member 53 using the magnetic force by this rotating magnetic field as a driving source, so as to project the injection needle 56. That is, the dome member 54 projects the injection needle 56 from the opening 54a using the magnetic force by this rotating magnetic field as a driving source.

Accordingly, as described above, the fifth embodiment of this invention is configured to include the casing that is a movable terminal whose one end slides in a longitudinal direction, and controls this movable terminal to slide so as to project the injection needle therein. Further, a helical projection member to be engaged with unevenness of the alimentary tract is provided on the external wall surface of this casing. The helical projection member is rotatably driven together with this casing so as to press this casing onto the desired part in the subject using the magnetic force of a rotating magnetic field generated outside this casing. At the same time, the movable terminal of this casing slides so as to project the injection needle from the casing. Thus, the casing can be fixed to the desired part in the subject, and the injection needle can be projected to the outside of the casing, with the magnetic force by the rotating magnetic field as one driving source. This gives the same functional effect as the above-described first embodiment, and this realizes the body-insertable apparatus that can be led toward details of the desired part, such as the diseased part, etc.

Descriptions will now be made to a sixth embodiment of this invention. A body-insertable apparatus according to the sixth embodiment is driven by pressure of fluid, such as medical agent, etc. as one driving source, and functions for injecting an injection needle by this driving source and fixing casing to a desired part in the subject.

Figure 23:
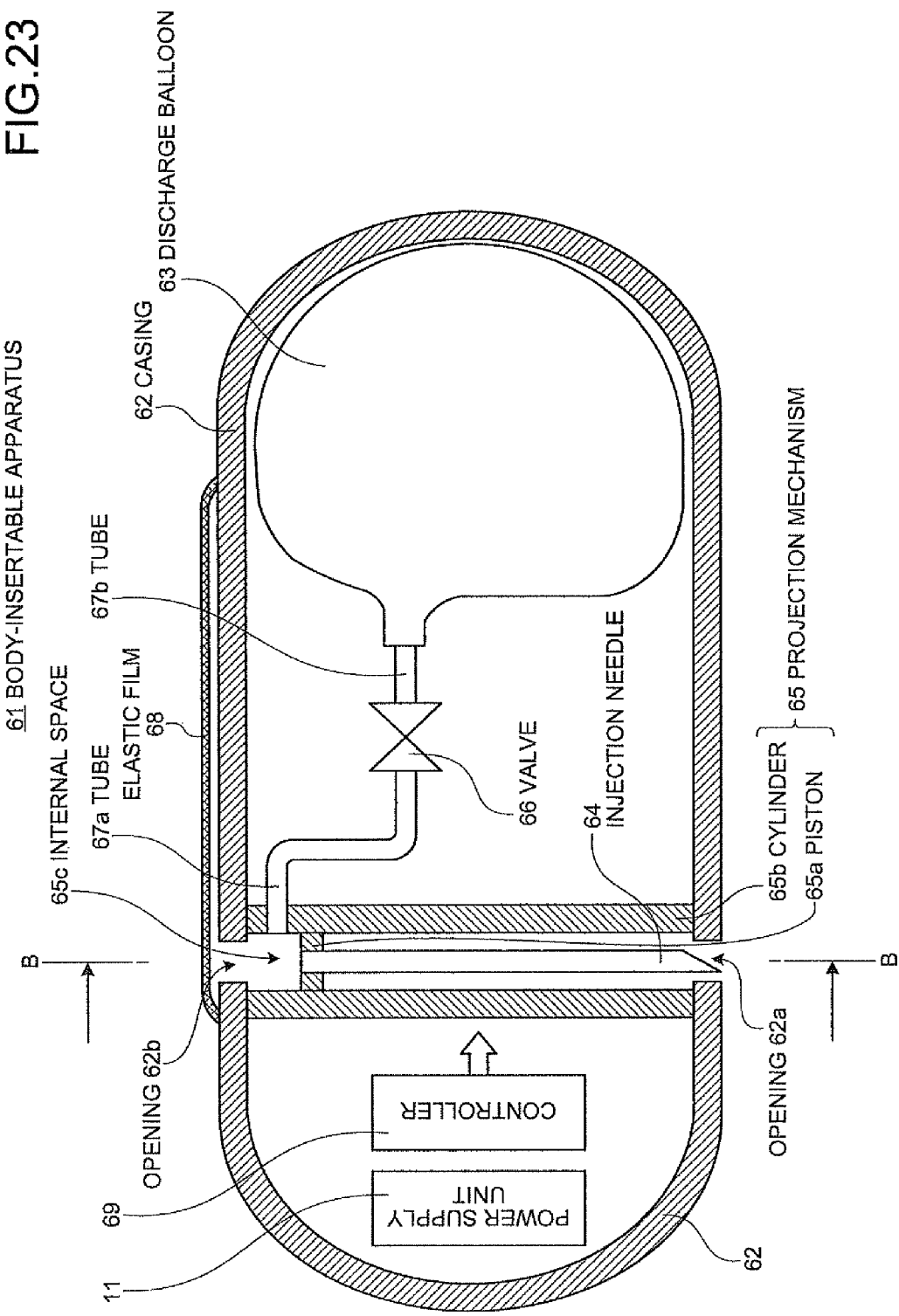
FIG. 23 is a schematic cross sectional view schematically showing a configuration example of a body-insertable apparatus as a sixth embodiment of this invention.
Figure 24:
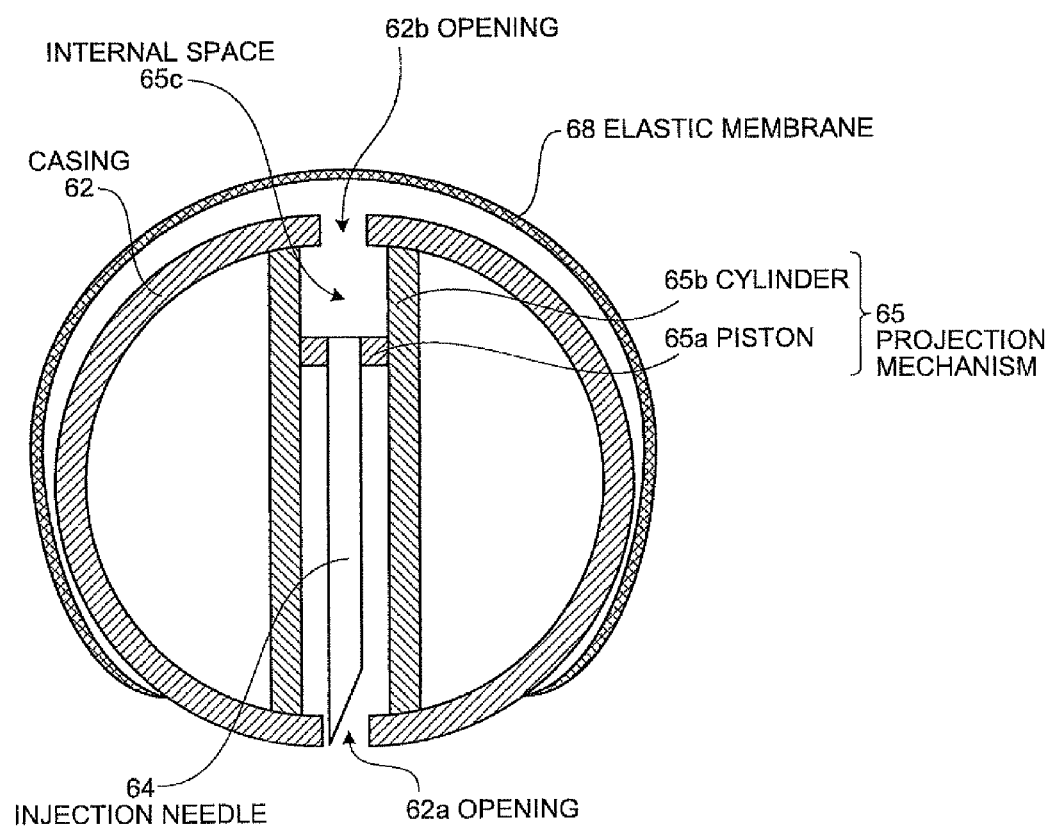
FIG. 24 is a schematic cross sectional view taken along line B-B of the body-insertable apparatus shown in FIG. 23.

FIG. 23 is a schematic cross sectional view schematically showing a configuration example of the body-insertable apparatus as the sixth embodiment of this invention. FIG. 24 is a schematic cross sectional view taken along a line B-B of the body-insertable apparatus shown in FIG. 23. As shown in FIG. 23 and FIG. 24, this body-insertable apparatus 61 includes a local injection mechanism for injecting medical agent inside capsule-type casing 62 with such a size as to easily be introduced into a subject, and includes fixing means for fixing the casing 62 to the desired part in the subject on the external wall surface of this casing 62.

Specifically, the body-insertable apparatus 61 has an elastic membrane 68 which expands by pressure of fluid as a driving source so as to fix the casing 62 to the desired part in the subject, on the external wall surface of the casing 62. The body-insertable apparatus 61 has a discharge balloon 63, an injection needle 64 and a projection mechanism 65, inside this casing 62. The discharge balloon 63 is to form a storage chamber for storing medical agent and discharges the medical agent. The injection needle 64 injects the medical agent discharged by the discharge balloon 63 to the desired part in the subject. The projection mechanism 65 projects the injection needle from the casing 62. The body-insertable apparatus 61 has a valve 66, a tube 67a and a tube 67b. The valve 66 is open/close-driven in order to begin or stop an operation for discharging medical agent by the discharge balloon 63. The tube 67a forms a circulation pipeline for medical agent circulating through the valve 66 and the projection mechanism 65. The tube 67b forms a circulation pipeline for medical agent circulating through the discharge balloon 63 and the valve 66. Further, the body-insertable apparatus 61 has a controller for controlling the open/close driving of the valve 66 and a power supply unit 11 for supplying the controller 69 with driving power.

As described above, the casing 62 is capsulate-type armored casing with such a size as to easily be introduced into a subject, and includes an opening 62a for projecting injection needle 64 and an opening 62b for connecting each of internal spaces of the projection mechanism 65 and the elastic membrane 68.

The discharge balloon 63 is realized with an elastic member, such as rubber, etc., and expands upon injection of medical agent, and contains medical agent while maintaining this expansion state. In this case, the discharge balloon 63 functions for discharging this contained medical agent by its contraction force which is potential to it due to this expansion. Specifically, the discharge balloon 63 is connected to the valve 66 through the tube 67b, contracts when the valve 66 is open-driven, and performs an operation for discharging medical agent upon application of pressure to the medical agent using its contraction force. The discharge balloon 63 stops to contract when the valve 66 is close-driven, and stops the operation for discharging medical agent.

The projection mechanism 65 functions as projection means for projecting the injection needle 64 to the outside of the casing 62 by the pressure of predetermined fluid as a driving source, for example, by the pressure of medical agent discharged by the discharge balloon 63. Specifically, the projection mechanism 65 is realized with a piston 65a on which the base end of the injection needle is mounted and a cylinder 65b for slidably storing this piston 65a.

The piston 65a on which the base end of the injection needle is mounted slides inside the cylinder 65b by the pressure of medical agent flowing to the cylinder 65b, and projects the injection needle 64 from the casing 62 through the opening 62a. This injection needle 64 includes a line for connecting an end side (pointed side) puncturing the subject and the base end side, and is fixed in the piston 65a in a state where this line is not closed.

The cylinder 65b slidably stores the piston 65a on which the injection needle 64 is mounted. One end of this cylinder 65b is so fixed on the internal wall of the casing 62 (specifically, the periphery of the opening 62a) that the path of this injection needle 64 corresponds to the opening 62a, while the other end thereof is so fixed on the internal wall of the casing 62 (specifically, the periphery of the opening 62b) that the opening 62b is positioned in a range surround by the internal wall of the cylinder 65b. In this case, an internal space 65c formed from the piston 65a, the cylinder 65b and the casing 62 near the opening 62b is connected to an internal area of the elastic membrane 68 through the opening 62b. This internal space 65c is connected to the valve 66 through the tube 67a. Such a cylinder 65b controls the sliding direction of the piston 65a such that the injection needle 64 is inserted to the opening 62a so as to project from the casing 62.

The valve 66 is open/close-driven under the control of the controller 69, and adjusts a connection state between the discharge balloon 63 and the cylinder 65b through the tubes 67a and 67b. Specifically, the valve 66 is open-driven so as to connect the discharge balloon 63 and the cylinder 65b, and causes the discharge balloon 63 to begin an operation for discharging medical agent. The valve 66 is close-driven so as to interrupt the connection between the discharge balloon 63 and the cylinder 65b and stop the operation for discharging medical agent by the discharge balloon 63.

The elastic membrane 68 expands by the pressure of fluid (e.g., pressure of medical agent) as a driving source, thereby functioning as fixing means for fixing the casing 62 in the desired part in the subject. Specifically, the elastic membrane 68 is realized with an elastic member, such as rubber, silicone resins, etc., and is so provided as to cover the external wall surface of the casing 62, excluding the injection-needle projecting side near the opening 62a, as shown, for example, in FIG. 23 and FIG. 24. In this case, the elastic membrane 68 is so provided as to cover the external wall surface of the casing 62, excluding both ends of the casing 62 and the injection-needle projecting side of the casing 62 (i.e. the side wall surface of the casing 62 pressed against the wall of the alimentary tract when the injection needle 64 is stuck into the desired part in the subject). The internal area formed from such an elastic membrane 68 and the external wall surface of the casing 62 (the internal area of the elastic membrane 68) is connected to the internal space 65c of the cylinder 65b through the opening 62b, and expands by the pressure of medical agent (i.e. pressure of medical agent discharged by the discharge balloon 63) flowing through the opening 62b as a driving source, and presses the injection-needle projecting side of the casing 62 against the wall of the alimentary tract in the subject. As described above, the elastic membrane 68 fixes the casing 62 to the desired part in the subject.

The controller 69 is to control the open/close driving of the valve 66. Specifically, the controller 69 controls the valve 66 to be open-driven so as to control the discharge balloon 63 to begin the operation for discharging medical agent, when the body-insertable apparatus 61 introduced into the subject has reached the desired part in the subject. The controller 69 controls the valve 66 to be close-driven so as to control the discharge balloon 63 to stop the operation for discharging the medical agent. Accordingly, the controller 69 controls the operation for discharging the medical agent by the discharge balloon through the controlling of the valve 66 to be open/close-driven. In this case, the projection mechanism 65 projects the injection needle 64 from the casing 62 by the pressure of medical agent discharged by the discharge balloon 63 as a driving source, and the elastic membrane 68 expands by the pressure of this medical agent as a driving source and fixes the casing 62 to the desired part in the subject. That is, the controller 69 controls the operation for projecting the injection needle 64 by the projection mechanism 65 and the operation for fixing the casing 62 by the elastic membrane 68, through the controlling of the valve 66 to be open/close-driven.

In a configuration for setting the timing for the controller 69 to control the valve 66 to be driven, a timer mechanism may be included, or a radio receiving mechanism may be included and an external control signal may be supplied to the controller 69.

Descriptions will now be made to a medical agent injection method according to the sixth embodiment of the present invention. According to the medical agent injection method for injecting medical agent into a desired part in the subject using the body-insertable apparatus 61 according to the sixth embodiment, along with approximately the same processing steps as the above-described steps S201 to S203 shown in FIG. 8, it is introduced into the desired part in the subject (introduction step), it is fixed to this desired part so as to project the injection needle 64 (fixing/projection step), thereafter injecting medical agent into this desired part (injection step). In this processing step of the body-insertable apparatus 61, the fixing/projection step differs from that of the above-described the second embodiment.

Specifically, the body-insertable apparatus 61 is fixed to the desired part in the subject, and projects the injection needle 64 to this desired part, by the pressure of medical agent discharged by the discharge balloon 63 as a driving source, in this fixing/projection step. In this case, the body-insertable apparatus 61 causes the elastic membrane 68 to expand so as to fix the casing 62 to the desired part in the subject, controls the piston 65a to slide toward the opening 62a so as to project the injection needle 64 from the casing 62, using the pressure of medical agent as a driving source.

Figure 25:
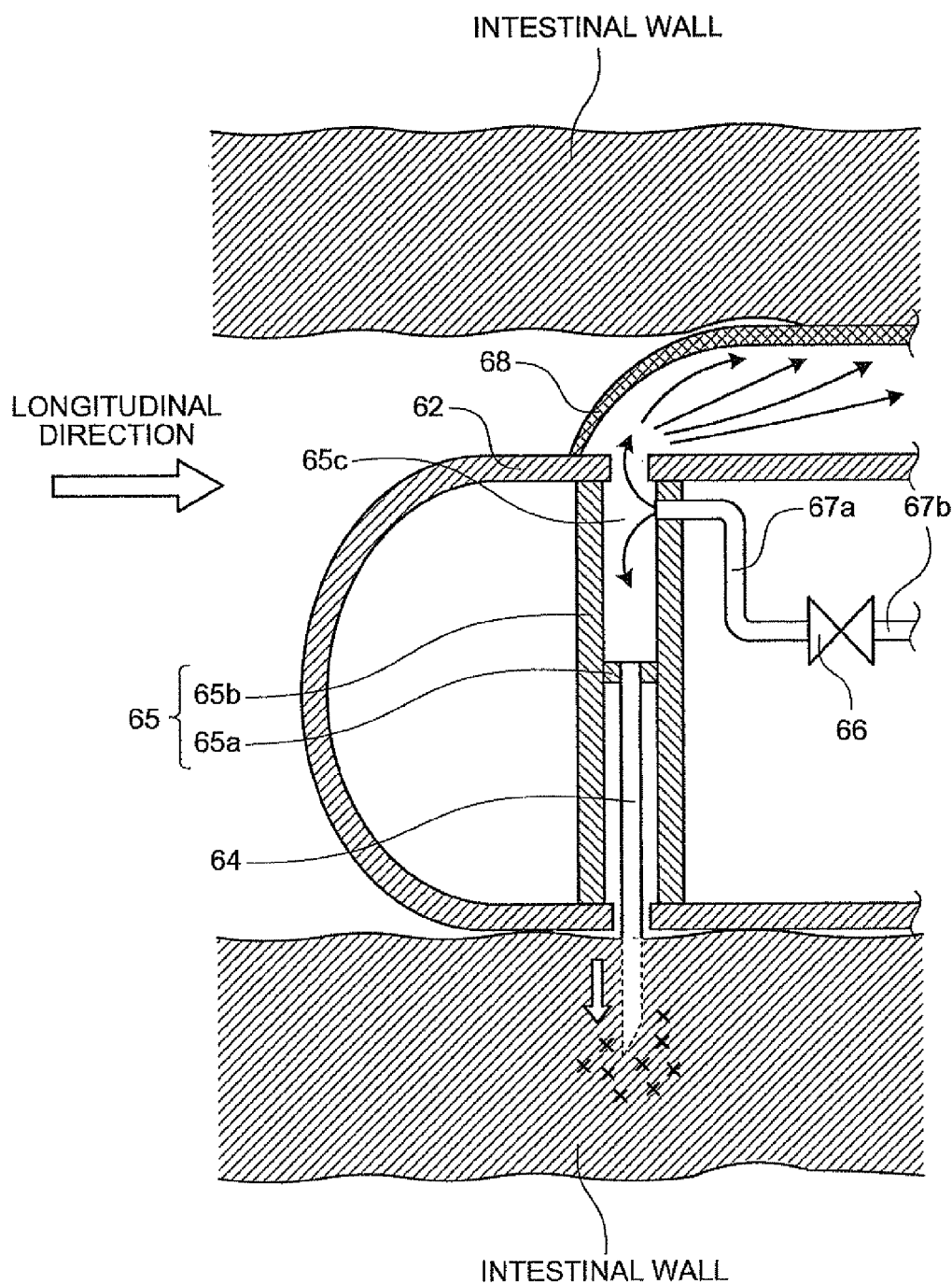
FIG. 25 is a schematic cross sectional view for explaining a fixing operation for casing by fluid pressure as one driving source and a projection operation for an injection needle.
Figure 26:
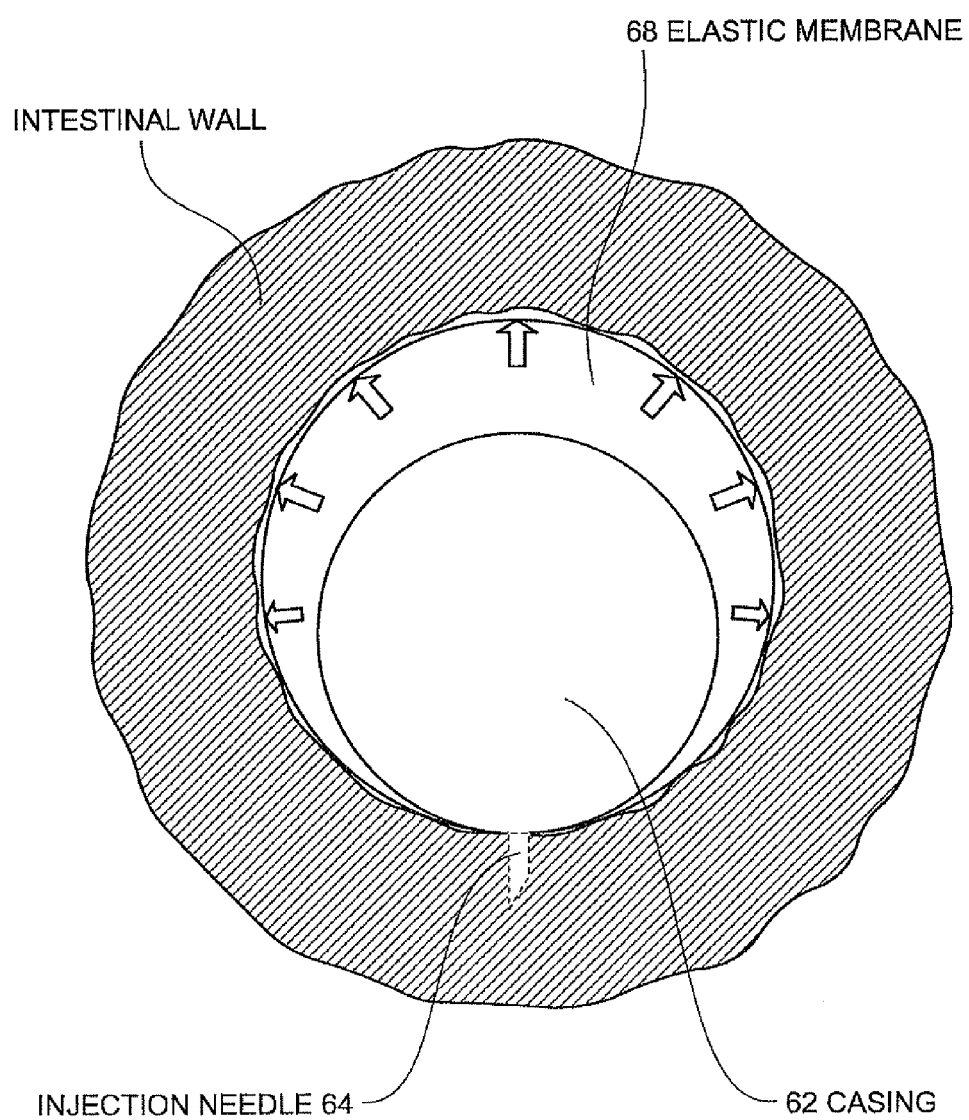
FIG. 26 is a front schematic diagram showing the body-insertable apparatus shown in FIG. 25, viewed from the longitudinal direction.
Figure 27:
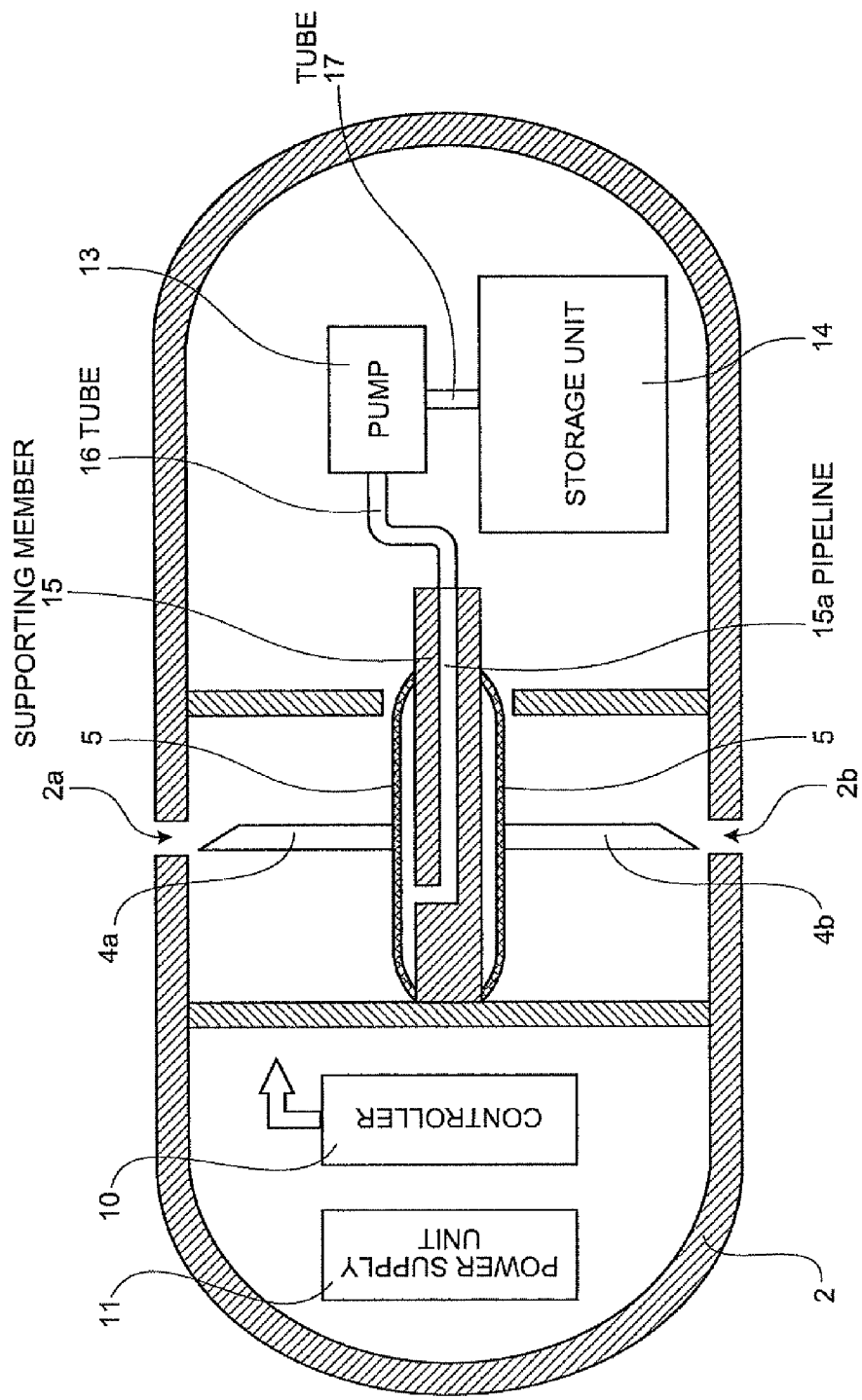
FIG. 27 is a schematic cross sectional view schematically showing a configuration example of a body-insertable apparatus as a modification of the first embodiment of this invention.

Descriptions will now be made to an operation for fixing the casing 62 by the elastic membrane 68 and an operation for protecting the injection needle 64 by the projection mechanism 65. FIG. 25 is a schematic cross sectional view for explaining the operation for fixing the casing 62 and the operation for projecting the injection needle, by the pressure of fluid as one driving source. FIG. 26 is a front schematic diagram of the body-insertable apparatus 61 shown in FIG. 25, viewed from the longitudinal direction. Descriptions will now be made to the operation for fixing the casing 62 by the elastic membrane 68 and the operation for projecting the injection needle 64 by the projection mechanism 65, with reference to FIG. 25 and FIG. 26.

When the body-insertable apparatus 61 introduced into the subject has reached the desired part in the subject, the controller 69 controls the valve 66 to be open-driven. When the valve 66 is open-driven under this control of the controller 69, the discharge balloon 63 and the cylinder 65a will return into a connection state through the valve 66 and the tubes 67a and 67b. In this case, the discharge balloon 63 begins the operation for discharging medical agent by its contraction force. The medical agent discharged by such a discharge balloon 63 flows into the internal space 65c of the cylinder 65b through the valve 66 and the tubes 67a and 67b.

The projection mechanism 65 performs the operation for projecting the injection needle by the pressure of medical agent thus flowed into the internal space 65c as a driving source. In this case, the piston 65a slides inside the cylinder 65b by the pressure of medical agent flowed into this internal space 65c as a driving source, and projects the injection needles 64 through the opening 62a.

In cooperation with this operation for projecting the injection needle 64 by this projection mechanism 65, the elastic membrane 68 performs the operation for fixing the casing 62 by the pressure of medical agent discharged by the discharge balloon 63 as a driving source 62. Specifically, the medical agent discharged into the internal space 65c by the discharge balloon 63 flows into the internal space of the elastic membrane 68 through the opening 62b. The elastic membrane 68 expands in the radial direction of the alimentary tract in the subject, such as the small intestine or large intestine, etc. by the pressure of medical agent flowed into the internal area as a driving source, and presses the external wall surface of the casing 62 on the injection-needle projecting side against the wall of the alimentary tract in the subject. As described, the elastic membrane 68 fixes the casing 62 to the desired part in the subject.

In this case, the elastic membrane 68 expands in the radial direction of the alimentary tract and presses the casing 62 against the wall of the alimentary tract, thereby preventing movement of the casing 62 into the desired part in the subject. Thus, the projection mechanism 65 can easily be stuck into the desired part in the subject using the injection needle 64, while resisting a reaction from the wall of the alimentary tract toward the injection needle 64 when the injection needle 64 pierces and/or pushes there, as shown in FIG. 25 and FIG. 26.

When the injection needle 64 thus punctures the desired part in the subject, the medical agent discharged by the discharge balloon 63 is injected to the desired part in the subject through the internal space 65c and the injection needle 64, etc. This state where the medical agent is injected to this desired part remains until the contraction force of the discharge balloon 63 will be zero, or until the valve 66 is close-driven under the control of the controller 69. As a result, a desired amount of medical agent can be injected to the desired part in the subject.

In the sixth embodiment of this invention, the injection needle 64 is projected and the casing 62 is fixed to the desired part in the subject by the pressure of medical agent discharged by the discharge balloon 63 as one driving source. However, the present invention is not limited to this. Liquid other than medical agent may flow into the internal space 65c and the internal area of the elastic membrane 68 through the opening 62b, the injection needle 64 may be projected by the pressure of this liquid as one driving source, and the elastic membrane 68 may expand so as to fix the casing. Gas generated by a blowing agent, etc. may flow into the internal space 65c and the internal area of the elastic membrane 68 through the opening 62b, the injection needle 64 may be projected by the pressure of this gas as one driving source, and the elastic membrane 68 may expand so as to fix the casing 62. In any case, the apparatus may be so configured that a flow mechanism for causing liquid or gas for generating this driving source to flow into the internal space 65c is further provided, and the tube 67a and the line of the injection needle 64 are directly connected to each other, thereby circulating the medical agent discharged by the discharge balloon 63 directly into the injection needle 64 without going through the internal space 65c.

In the sixth embodiment of this invention, the injection needle is fixed to the piston slidably provided inside the cylinder, and the injection needle is projected upon sliding of this piston by the pressure of medical agent. However, this invention is not limited to this, and may further include a spring between the projection part of the injection needle and the piston, and may store the injection needle inside the casing by elasticity of this spring.

Accordingly, as described above, in the sixth embodiment of this invention, the piston on which the injection needle is fixed slides by the pressure of fluid so as to project the injection from the casing, and the elastic membrane provided on the external wall surface of the casing expands by the pressure of fluid so as to press the casing against the wall of the alimentary tract in the subject. Thus, the casing can be fixed to the desired part in the subject, and the injection needle can be projected to the outside of the casing by the pressure of fluid, such as liquid (e.g. medical agent) or gas as one driving source. This gives the same functional effect as that of the above-described the first embodiment, and this can realize the body-insertable apparatus which can prevent movement of the casing without unintentionally puncturing the alimentary tract when to puncture the desired part in the subject.

In the first to the sixth embodiments of this invention, the discharge balloon has been used as medical agent discharge means for discharging medical agent stored inside the casing. However, the present invention is not limited to this, and may use a storage unit, such as a tank, etc. for storing medical agent and a pump for discharging the medical agent from this storage unit, in place of the above-described discharge balloon. For example, the body-insertable apparatus according to the first embodiment may include a pump 13 and a storage unit 14 for medical agent in place of the discharge balloon 3, and may include a supporting member 15 including a pipeline 15a formed therein in place of the supporting member 8. Specifically, in a body-insertable apparatus 18 as a modification of the first embodiment, the internal space of the balloon 5 is connected to the pump 13 through a tube 16 and the pipeline 15a, and the pump 13 is connected to the storage unit 14 through a tube 17. The body-insertable apparatus 18 can circulate the medical agent stored in the storage unit 14 into the internal space of the balloon 5 by driving of the pump 13 under the control of the controller 10, thus giving the same functional effect as that of the above-described the first embodiment.

Figure 28:
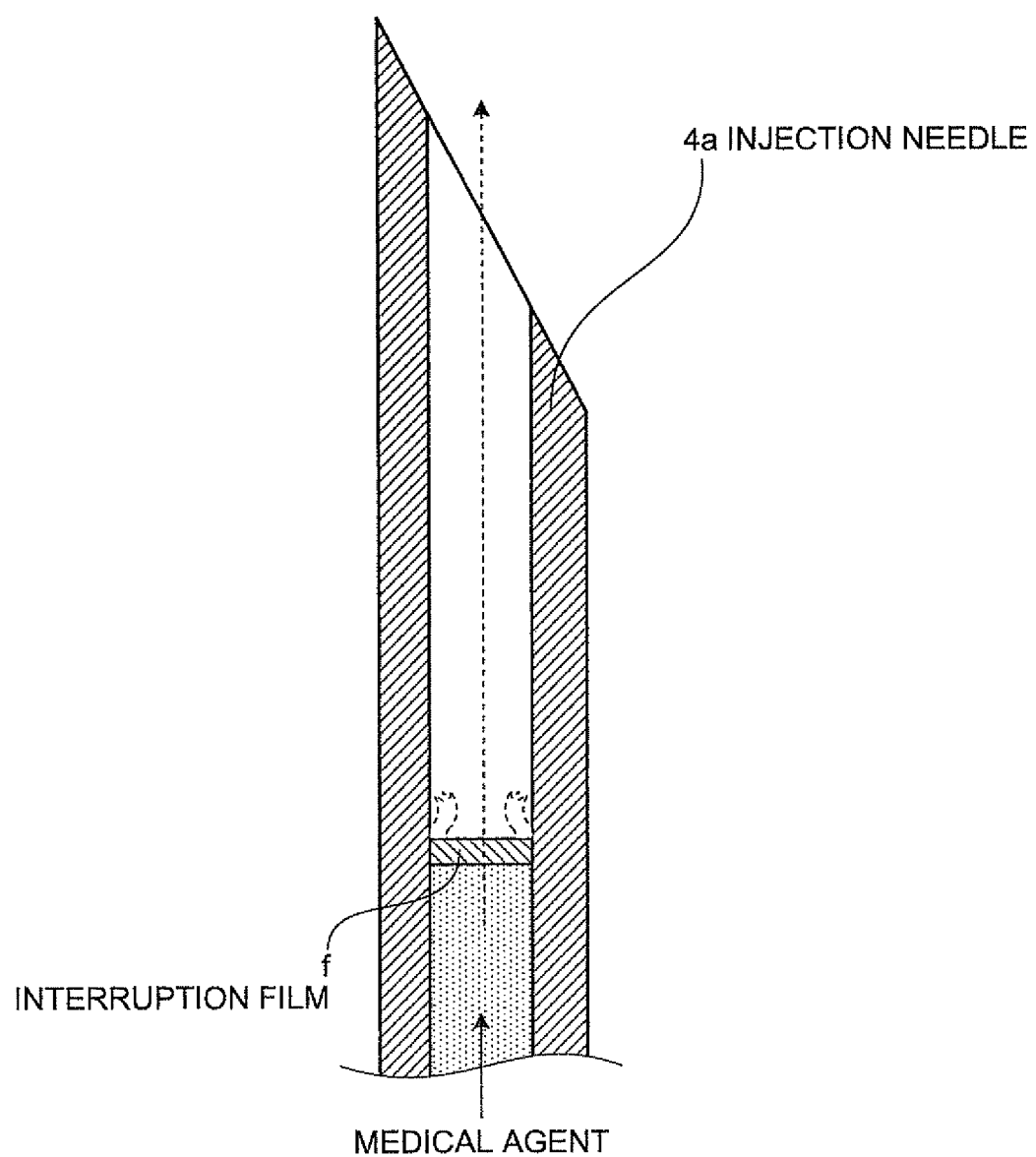
FIG. 28 is a schematic cross sectional view schematically showing a modification of an injection needle provided in the body-insertable apparatus of this invention.

The first to the sixth embodiments of this invention use the injection needle including the line formed therein and connecting the end side (having the pointed form) and the base end side. However, this invention is not limited to this, and may further include an interruption film for temporarily interrupting circulation of medical agent, in the line formed thereinside. As the injection needle 4a shown in FIG. 28, such an injection needle includes an interruption film f to be fractured by the pressure of a predetermined value or greater inside this line, so as to temporarily interrupt external circulation of medical agent flowed into this pipeline. In this case, the interruption film f can temporarily stop the discharge of medical agent from the injection needle 4a, in a period since the operation for projecting the injection needle 4a begins until the injection needle 4a is stuck into the desired part in the subject. This can prevent leakage of medical agent to be wasted, when the injection needle pierces and/or pushes the desired part in the subject.

Further, in the body-insertable apparatus according to any of the first to the sixth embodiments, the discharge of medical agent is temporarily interrupted, thereby further increasing the pressure of medical agent used as a driving source for the operation for fixing the casing and reliably fixing the casing to the desired part in the subject.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A body-insertable apparatus comprising:
    a capsule-type casing which is adapted to be swallowed into a subject;
    a discharge balloon which possesses a self-contraction force and stores a medical agent;
    a projecting balloon which connects with the discharge balloon;
    at least one injection needle being connected with the projecting balloon;
    a valve which opens and closes between the discharge balloon and the projecting balloon; and,
    a controller which controls, by opening and closing the valve, an injection operation that injects the medical agent by a contraction of the discharge balloon, a projection operation that projects the at least one injection needle to the outside of the capsule-type casing by an expansion of the projecting balloon when the medical agent flows into the projecting balloon from the discharge balloon, and a storing operation that stores the at least one injection needle inside the capsule-type casing by a contraction of the projecting balloon.

2. The body-insertable apparatus according to claim 1, wherein a plurality of the injection needles are arranged on the projecting balloon, and a same angle is formed between each of the injection needles and a center axis of the body-insertable apparatus, the same angle being 90 degrees or more.

3. The body-insertable apparatus according to claim 1, further comprising:
    a shape memory member for opening and closing the valve to adjust a connection state between the discharge balloon and the projecting balloon, wherein
    the controller supplies an electric current to the shape memory member for changing the shape of the shape memory member to open and close the valve.

4. The body-insertable apparatus according to claim 1, further comprising a supporting member which is installed inside of the projecting balloon and supports the projecting balloon.

5. The body-insertable apparatus according to claim 1, wherein
    the at least one injection needle comprises a first injection needle which is projected in a radial direction of the capsule-type casing;
    and a second injection needle which is projected in a different radial direction of the capsule-type casing.

6. A body-insertable apparatus comprising:
    a capsule-type casing which is adapted to be swallowed into a subject;
    a discharge balloon disposed in the casing, the discharge balloon storing a medical agent internally therein;
    a projecting balloon disposed in the casing, the projecting balloon being in fluid communication with the discharge balloon;
    an injection needle movably disposed in the casing between a stored position within the casing and a projecting position in which at least a portion of the injection needle projects from an outer surface of the casing, the injection needle further being connected to and movable with the projecting balloon;
    a valve which opens and closes the fluid communication between the discharge balloon and the projecting balloon;
    and, a controller configured to control, by opening and closing the valve, an injection operation that injects the medical agent by a contraction of the discharge balloon, a projection operation to move the injection needle from the stored position to the projecting position by an expansion of the projecting balloon when the medical agent flows into the projecting balloon from the discharge balloon, and a storing operation to move the injection needle from the projecting position to the stored position by a contraction of the projecting balloon.

* * * * *